(12) United States Patent
Ren et al.

(10) Patent No.: US 11,891,737 B2
(45) Date of Patent: *Feb. 6, 2024

(54) AIRLAID COMPOSITE SHEET MATERIAL AND METHOD

(71) Applicants: Fitesa (China) Airlaid Company Limited, Tianjin (CN); Fitesa Simponsville, Inc., Simponsville, SC (US)

(72) Inventors: Jichun Ren, Tianjin (CN); Juan Wang, Tianjin (CN); Xunwang Feng, Tianjin (CN); Yijian Qu, Tianjin (CN); Marc Newman, Simponsville, SC (US)

(73) Assignees: Fitesa (China) Airlaid Company Limited, Tianjin (CN); Fitesa Simpsonville, Inc., Simpsonville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/585,379

(22) Filed: Jan. 26, 2022

(65) Prior Publication Data

US 2022/0178059 A1 Jun. 9, 2022

Related U.S. Application Data

(63) Continuation of application No. 16/606,103, filed as application No. PCT/IB2017/056511 on Oct. 19, 2017, now Pat. No. 11,268,220.

(30) Foreign Application Priority Data

Apr. 26, 2017 (CN) .......................... 201710284171.5

(51) Int. Cl.
*D04H 1/732* (2012.01)
*A61F 13/472* (2006.01)
(Continued)

(52) U.S. Cl.
CPC .......... *D04H 1/732* (2013.01); *A61F 13/472* (2013.01); *A61F 13/49* (2013.01); *B32B 3/30* (2013.01);
(Continued)

(58) Field of Classification Search
CPC ...... D04H 1/732; D04H 1/5412; D04H 1/559; A61F 13/472; A61F 13/49; B32B 3/30;
(Continued)

(56) References Cited

U.S. PATENT DOCUMENTS 3,708,361 A * 1/1973 Stumpf .................. D04H 11/08
156/72
4,559,050 A * 12/1985 Iskra ..................... A61F 13/511
604/379

(Continued)

FOREIGN PATENT DOCUMENTS

CN 1119581 A 4/1996
CN 1617696 A 5/2005
(Continued)

OTHER PUBLICATIONS

English machine translation of JP2016195753A, Nov. 24, 2016, Katsumata, 16 pages. (Year: 2016).*

(Continued)

*Primary Examiner* — Linda L Gray

(57) ABSTRACT

Provided is a composite sheet that is particularly useful as an AQDL component in absorbent articles. The composite sheet includes a fluid acquisition component and an airlaid component. The airlaid component may include one or more airlaid layers that are successively formed overlying each other. Each of the airlaid layers are adjacent to, and in direct contact with, immediately adjacent layers of the airlaid component so that adjacent layers are in fluid communication with respect to each other. The fluid acquisition com- (Continued)

ponent includes a nonwoven fabric comprising a carded nonwoven fabric comprised of a plurality of staple fibers that are air through bonded to each other to form a coherent nonwoven fabric. The airlaid layer(s) include a blend of cellulose and non-cellulose staple fibers. The staple fibers may be bicomponent fibers having a polyethyelene sheath and a polypropylene or polyethylene terephthalate core, and mixtures of such fibers.

19 Claims, 9 Drawing Sheets

(51) Int. Cl.
| | | |
|---|---|---|
| *B32B 3/30* | (2006.01) | |
| *B32B 37/06* | (2006.01) | |
| *B32B 38/06* | (2006.01) | |
| *D06N 3/00* | (2006.01) | |
| *D04H 1/541* | (2012.01) | |
| *A61F 13/49* | (2006.01) | |
| *B32B 5/02* | (2006.01) | |
| *B32B 5/26* | (2006.01) | |
| *D04H 1/559* | (2012.01) | |
| *B32B 38/00* | (2006.01) | |
| *B32B 37/24* | (2006.01) | |

(52) U.S. Cl.
CPC ............... *B32B 5/022* (2013.01); *B32B 5/26* (2013.01); *B32B 37/06* (2013.01); *B32B 38/06* (2013.01); *B32B 38/164* (2013.01); *D04H 1/5412* (2020.05); *D04H 1/559* (2013.01); *D06N 3/0011* (2013.01); *D06N 3/0013* (2013.01); *D06N 3/0036* (2013.01); *D06N 3/0038* (2013.01); *B32B 2037/243* (2013.01); *B32B 2255/02* (2013.01); *B32B 2255/26* (2013.01); *B32B 2262/0253* (2013.01); *B32B 2262/0276* (2013.01); *B32B 2262/062* (2013.01); *B32B 2262/12* (2013.01); *B32B 2307/726* (2013.01); *B32B 2309/10* (2013.01); *B32B 2310/0454* (2013.01); *B32B 2319/00* (2013.01); *B32B 2323/04* (2013.01); *B32B 2323/10* (2013.01); *B32B 2367/00* (2013.01); *B32B 2555/02* (2013.01); *D06N 2201/042* (2013.01); *D06N 2209/126* (2013.01); *D06N 2211/24* (2013.01)

(58) Field of Classification Search
CPC ........... B32B 5/022; B32B 5/26; B32B 37/06; B32B 38/06; B32B 38/164; D06N 3/0011; D06N 3/0013; D06N 3/0036; D06N 3/0038
See application file for complete search history.

(56) References Cited

U.S. PATENT DOCUMENTS

| | | | | |
|---|---|---|---|---|
| 5,114,787 A | * | 5/1992 | Chaplin | .................. B32B 27/12 |
| | | | | 156/308.2 |
| 5,399,174 A | * | 3/1995 | Yeo | .......................... D04H 3/12 |
| | | | | 604/366 |
| 5,470,640 A | * | 11/1995 | Modrak | ................... D04H 1/74 |
| | | | | 428/218 |
| 5,494,736 A | * | 2/1996 | Willey | .................. D04H 1/5412 |
| | | | | 602/45 |
| 6,383,609 B1 | * | 5/2002 | Annergren | .............. A61L 15/28 |
| | | | | 428/297.4 |
| 6,479,415 B1 | | 11/2002 | Erspamer et al. | |
| 6,488,670 B1 | | 12/2002 | Schild et al. | |
| 11,268,220 B2 | * | 3/2022 | Ren | ........................ D04H 1/559 |
| 2001/0039405 A1 | | 11/2001 | Keuhn, Jr. et al. | |
| 2008/0217809 A1 | | 9/2008 | Zhao et al. | |
| 2009/0001118 A1 | | 1/2009 | Habeck et al. | |
| 2009/0011188 A1 | | 1/2009 | Yasumitsu et al. | |
| 2009/0204095 A1 | | 8/2009 | McDaniel | |
| 2013/0101805 A1 | | 4/2013 | Altshuler et al. | |
| 2014/0121621 A1 | | 5/2014 | Kirby et al. | |
| 2015/0342802 A1 | | 12/2015 | Caputi et al. | |

FOREIGN PATENT DOCUMENTS

| | | | | |
|---|---|---|---|---|
| CN | 1732083 A | | 2/2006 | |
| CN | 1823189 A | | 8/2006 | |
| CN | 101085865 A | | 12/2007 | |
| CN | 101115453 A | | 1/2008 | |
| CN | 101528169 A | | 9/2009 | |
| CN | 101854820 A | | 10/2010 | |
| CN | 103042747 A | | 4/2013 | |
| CN | 203513968 U | | 4/2014 | |
| CN | 104540988 A | | 4/2015 | |
| CN | 104994821 A | | 10/2015 | |
| EP | 0626159 A1 | * | 11/1994 | ............... D04H 3/14 |
| JP | 2003-113564 A | | 4/2003 | |
| JP | 2003-325411 A | | 11/2003 | |
| JP | 2007-031856 A | | 2/2007 | |
| JP | 2016-195753 A | | 11/2016 | |
| WO | WO95342264 | * | 12/1995 | |
| WO | 01/48291 A1 | | 7/2001 | |
| WO | WO03092757 A1 | * | 11/2003 | ............. B32B 27/18 |
| WO | 2013/056978 A2 | | 4/2013 | |
| WO | 2013175322 A1 | | 11/2013 | |

OTHER PUBLICATIONS

English machine translation of EP0626159A1, Nov. 30, 1994; Takai; 6 pages. (Year: 1994).*
English machine translation of abstract of JP01292180A, Nov. 1989, Sasaki, Nov. 1989, 1 page. (Year: 1989).*
Decision for a Patent for Japanese Patent Application No. 2019-559071 (3 pages).
English Translation of Notice of the Reasons for Rejection for Japanese Patent Application No. 2019-559071, dated Oct. 15, 2021 (9 pages).
European Search Report and Written Opinion for Application No. 17907418.2, dated Feb. 5, 2021 (12 pages).
Search Report for Chinese Application 2017800900488, dated Jul. 25, 2021.
Intention to Grant for Application No. 17907418.2, dated Nov. 22, 2021,.
Notice of the Reasons for Rejection for Patent Application No. 2019-559071.
Translation of Search Report for Chinese Application 2017800900488, dated Jul. 25, 2021.
First Examination Report dated Feb. 4, 2022, IN Patent Application No. 201917047813 (5 pages).
Second Office Action dated Jan. 24, 2022, CN Patent Application No. 201780090048.8 (14 pages).
English Translation of Second Office Action dated Jan. 24, 2022, CN Patent Application No. 201780090048.8 (27 pages).

* cited by examiner

AIRLAID COMPOSITE SHEET MATERIAL AND METHOD

CROSS REFERENCE TO RELATED APPLICATIONS

The present application claims the benefit of U.S. application Ser. No. 16/606,103, filed Oct. 17, 2019, which claims the benefit of International Application No. PCT/IB2017/056511, filed Oct. 19, 2017, which claims the benefit of Chinese Application No. 2017 10284171.5, filed Apr. 26, 2017, the contents of which are all hereby incorporated by reference.

FIELD

The present invention relates generally to a composite sheet material for use in absorbent articles, and more particularly, to a composite sheet material comprising a porous fluid acquisition layer and an airlaid layer comprising a blend of cellulose staple fiber and non-cellulose staple fibers.

BACKGROUND

Nonwoven composite sheets made with a combination of various natural fibers and synthetic fibers are known for use in the manufacture of absorbent articles. Such absorbent articles may include disposable hygiene products, such as diapers, women sanitary products, adult incontinent products, and the like.

Typical absorbent articles typically include a multilayer construction having an inner layer (also referred to as a top sheet) defining an inner surface that is in contact with the skin of the wearer, an acquisition/distribution layer (also referred to as an AQDL component) disposed underlying the top sheet, an absorbent layer comprising a material selected to absorb fluids, and an outer layer (also referred to as a back sheet) defining an outer surface of the article. Typically, the back sheet comprises a material that is impervious to fluids so that any fluids absorbed within the absorbent core do not escape or leak.

Materials typically used in the AQDL are typically selected to rapidly transport fluids from the top sheet and into the absorbent core. This rapid transport (also referred to herein as flash permeation) transports the fluid in the z-direction from the top sheet to the absorbent core. In order to prevent fluid from pooling or remaining near the skin of the wearer, it is important that the distribution layer prevents or reduces reverse osmosis of fluids from the absorbent core and back through the top sheet.

In general, many conventional materials used in the production of AQDLs have rapid fluid acquisition in the z-direction, but have undesirable lateral fluid distribution (x-direction and y-direction). As a result, fluids are quickly transported from the top sheet to the absorbent core, but are often not sufficiently distributed throughout the AQDL prior to being introduced into the absorbent core. This may cause the fluids to be localized in one region of the absorbent core, and result in prolonged exposure of the skin of the wearer to the fluid. Prolonged exposure to fluids is undesirable.

SUMMARY

Embodiments of the present invention are directed to a composite sheet that is particularly useful as a fluid AQDL component in absorbent articles. In one embodiment, a composite sheet is provided in which the composite sheet comprises a fluid acquisition component and an airlaid component overlying the fluid acquisition component. The airlaid component may comprise one or more airlaid layers that are successively formed overlying each other. Preferably, each of the airlaid layers are adjacent to, and in direct contact with, immediately adjacent layers of the airlaid component so that adjacent layers are in fluid communication with respect to each other.

In one embodiment, the fluid acquisition component comprises a nonwoven fabric comprising a carded nonwoven fabric comprised of a plurality of staple fibers that are air through bonded to each other to form a coherent nonwoven fabric. In one embodiment, the non-cellulose fibers comprise polymers derived from synthetic sources, and/or polymers derived from natural or sustainable sources, such as PLA. Preferred staple fibers for the carded nonwoven fabric comprise bicomponent fibers having a polyethyelene sheath and a polypropylene or polyethylene terephthalate core, and mixtures of such fibers.

In one embodiment, the airlaid component comprises at least one airlaid nonwoven layer comprising a homogenous mixture of cellulose and non-cellulose staple fibers that are deposited directly onto the surface of the fluid acquisition layer, or deposited directly onto a surface of a previously deposited airlaid layer. Advantageously, the air-layer may be thermally bonded to the fluid acquisition layer without the use of additional adhesives or the use of additional polymer powders and resins. Preferred non-cellulose staple fibers comprise bicomponent fibers having a polyethyelene sheath and a polypropylene or polyethylene terephthalate core, and mixtures of such fibers.

The cellulose staple fibers may comprise treated or untreated wood pulp. The non-cellulose staple fibers may comprise bicomponent or monocomponent fibers, or blends thereof. In one embodiment, the non-cellulose fibers comprise polymers derived from synthetic sources, and/or polymers derived from natural or sustainable sources, such as PLA.

In comparison with prior art materials, composite sheets in accordance with embodiments of the present invention may provide the advantages detailed below.

(1) The composite sheet material comprises nonwoven fabrics having good fluid flash-permeation and distribution properties. In certain embodiments, the composite sheet material comprises a fluid acquisition layer that can be thermally bonded with an airlaid component while still being capable of being used in subsequent conversion processes in the manufacture of absorbent articles.

(2) The composite sheet comprises an airlaid component comprising one or more airlaid layers may also provide an absorbent article that is more comfortable to a wearer of the absorbent article. For example, the airlaid component may comprise material that have a fluffy and soft feeling as well as low integral density. In addition, the materials for the fluid acquisition layer and the airlaid component may be selected to provide density gradient (e.g. lower to higher density in each successive layer) to assist in transporting a fluid quickly from the top sheet to the absorbent core.

(3) The fluid acquisition layer of the composite sheet may comprise a multi-pore structure having large average pore sizes and a relatively low density. As a result, the fluid acquisition layer may be capable of efficiently transporting a fluid from the top sheet, and into the airlaid component of the composite sheet.

(4) In some embodiments, the airlaid component comprises a relatively more compact structure having a smaller pore volume, and relatively higher densities. In addition, the airlaid component comprises cellulose fibers, which also helps to provide fluid absorption properties. The combination of these properties, helps to distribute a fluid quickly and broadly through-out the airlaid component, and to temporarily store fluid. This helps to efficiently transport and distribute the fluid through the airlaid layer prior to the fluid being transported into the absorbent core (5) The composite sheet material may also provide improved comfort to the wearer. In particular, embodiments of the composite sheet material may have good rebound resiliency in comparison to other materials used in absorbent articles. In particular, rebound resiliency measures the materials ability to return towards its original thickness after being subjected to a compression force. A higher rebound resiliency is indicative of the material's overall cushiony softness and comfort. In some embodiments, the thickness rebound resilience of articles in accordance with embodiments of the present invention after three months of aging under compression may be about 15 to 60% or more. In comparison, prior art materials, may have a rebound resilience that is 10% or less. This advantage may help enable the end product absorbent article to have a cushiony soft and fluffy feeling to the wearer.

(6) The composite sheet may also have very good anti-reverse osmosis performance, which results in the absorbent article having a dry-touch, and further improves the comfort of use by the wearer.

(7) The process of preparing the composite sheet also allows two kinds of fibers in the fiber layer to be homogeneously mixed and bonded to each other and to adjacent layers of the composite sheet. This may further improve the fluid distribution between layers, and through the composite sheet as whole. As a result, improved fluid distribution, diffusion, and absorption, resiliency, and anti-reverse osmosis properties may be obtained in the absorbent article.

(8) As noted previously, the composite sheet may also comprise a material having a density gradient when absorbing a fluid. As a result, the surface stain size of the composite sheet may be smaller, and as a result, an absorbed fluid can spread quickly when transporting through the fluid acquisition layer. This may help articles comprising the absorbent article to achieve small surface stain size when absorbing a fluid. The relatively larger liquid absorbing area in the airlaid component, helps the absorbent articles (e.g., sanitary napkins) to have much smaller surface visual effect, which may also help to provide the good reverse osmosis performance of the composite sheet.

(9) Finally, the distribution and flash-permeation of the composite sheet is improved in comparison to other materials, the anti-reverse osmosis effect is good, and as a powder binding agent and additional polymer resins beyond the compositions of the fibers are not required to join the fluid distribution component and the airlaid component, the composite sheet is much softer and fluffier than materials provided in the prior art.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
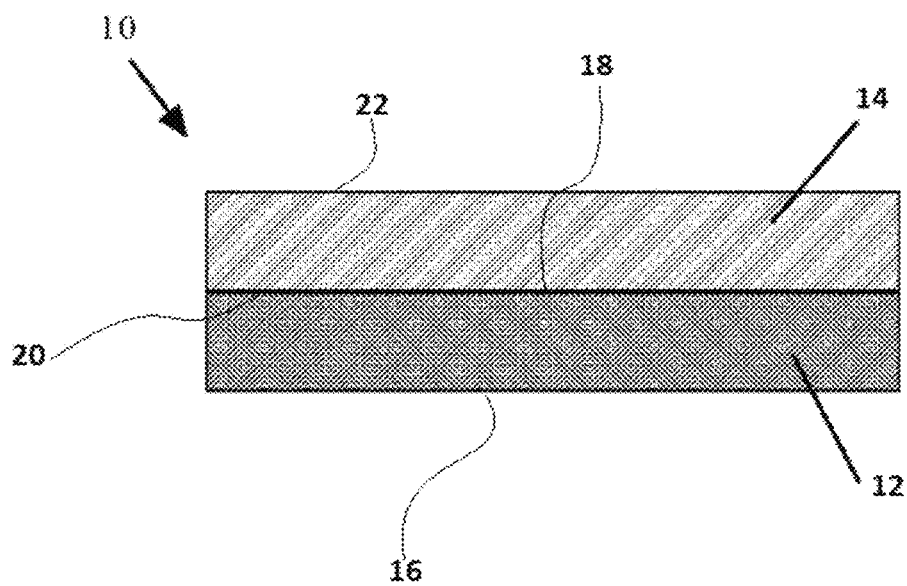
FIG. 1 is a cross-sectional side view of a composite sheet in accordance with at least one embodiment of the present invention.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

DEFINITIONS

For the purposes of the present application, the following terms shall have the following meanings:

The term "fiber" can refer to a fiber of finite length or a filament of infinite length.

The term "staple fiber" refers to a fibers of finite length. In general staple fibers may have a length from about 2 to 200 millimeters (mm).

As used herein, the term "monocomponent" refers to fibers formed from one polymer or formed from a single blend of polymers. Of course, this does not exclude fibers to which additives have been added for color, anti-static properties, lubrication, hydrophilicity, liquid repellency, etc.

As used herein, the term "multicomponent" refers to fibers formed from at least two polymers (e.g., bicomponent fibers) that are extruded from separate extruders. The at least two polymers can each independently be the same or different from each other, or be a blend of polymers. The polymers are arranged in substantially constantly positioned distinct zones across the cross-section of the fibers. The components may be arranged in any desired configuration, such as sheath-core, side-by-side, segmented pie, island-in-the-sea, and so forth. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference.

As used herein, the terms "nonwoven," "nonwoven web" and "nonwoven fabric" refer to a structure or a web of material which has been formed without use of weaving or knitting processes to produce a structure of individual fibers or threads which are intermeshed, but not in an identifiable, repeating manner. Nonwoven webs have been, in the past, formed by a variety of conventional processes such as, for example, meltblown processes, spunbond processes, and staple fiber carding processes.

As used herein, the term "carded fabric" refers to a nonwoven fabric comprising staple fibers that are predominantly aligned and oriented in the machine direction using a carding process.

As used herein, the term "meltblown" refers to a process in which fibers are formed by extruding a molten thermoplastic material through a plurality of fine, usually circular, die capillaries into a high velocity gas (e.g. air) stream which attenuates the molten thermoplastic material and forms fibers, which can be to microfiber diameter. Thereafter, the meltblown fibers are carried by the gas stream and are deposited on a collecting surface to form a web of random meltblown fibers. Such a process is disclosed, for example, in U.S. Pat. No. 3,849,241 to Buntin et al.

As used herein, the term "machine direction" or "MD" refers to the direction of travel of the nonwoven web during manufacturing.

As used herein, the term "cross direction" or "CD" refers to a direction that is perpendicular to the machine direction and extends laterally across the width of the nonwoven web.

As used herein, the term "spunbond" refers to a process involving extruding a molten thermoplastic material as filaments from a plurality of fine, usually circular, capillaries of a spinneret, with the filaments then being attenuated and drawn mechanically or pneumatically. The filaments are deposited on a collecting surface to form a web of randomly arranged substantially continuous filaments which can thereafter be bonded together to form a coherent nonwoven fabric. The production of spunbond non-woven webs is illustrated in patents such as, for example, U.S. Pat. Nos. 3,338,992; 3,692,613; 3,802,817; 4,405,297; and 5,665,300. In general, these spunbond processes include extruding the filaments from a spinneret, quenching the filaments with a flow of air to hasten the solidification of the molten filaments, attenuating the filaments by applying a draw tension, either by pneumatically entraining the filaments in an air stream or mechanically by wrapping them around mechanical draw rolls, depositing the drawn filaments onto a foraminous collection surface to form a web, and bonding the web of loose filaments into a nonwoven fabric. The bonding can be any thermal or chemical bonding treatment, with thermal point bonding being typical.

As used herein, the term "air through thermal bonding" involves passing a material such as one or more webs of fibers to be bonded through a stream of heated gas, such as air, in which the temperature of the heated gas is above the softening or melting temperature of at least one polymer component of the material being bonded. Air through thermal bonding may involve passing a material through a heated oven.

As used herein, the term "thermal point bonding" involves passing a material such as one or more webs of fibers to be bonded between a heated calender roll and an anvil roll. The calender roll is typically patterned so that the fabric is bonded in discrete point bond sites rather than being bonded across its entire surface.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material, including isotactic, syndiotactic and random symmetries.

The term "composite", as used herein, may be a structure comprising two or more layers, such as a film layer and a fiber layer or a plurality of fiber layers molded together. The two layers of a composite structure may be joined together such that a substantial portion of their common X-Y plane interface, according to certain embodiments of the invention.

Unless otherwise apparent from the context, the term "about" encompasses values within a standard margin of error of measurement (e.g., SEM) of a stated value or variations ±0.5%, 1%, 5%, or 10% from a specified value.

Embodiments of the invention are directed to a composite sheet material that is particularly useful in the manufacture of absorbent articles, and in particular, disposable feminine hygiene products and diaper products. As explained in greater detail below, the composite sheet material comprises a multilayer structure having a fluid acqustion layerand one or more airlaid layers that are successively deposited overlying the fluid acquisition layers. The airlaid layers comprise a blend of cellulose staple fibers and non-cellulose staple fibers that are selected to provide a fabric that is particularly suited for use as a fluid/acquisition layer in an absorbent article.

With reference to FIG. 1, a composite sheet material in accordance with at least one embodiment of the invention is shown and designated by reference character 10. In the illustrated embodiment, the sheet material comprises a fluid acquisition component 12 and an airlaid component 14 overlying the fluid acqustion component. The fluid acquisition component includes at least one nonwoven layer having a first outer surface 16 and a second outer surface 18. Similarly, the airlaid component includes a first outer surface 20 and a second outer surface 22.

In one embodiment, the outer surface 18 of the fluid acquisition is component 12 is disposed adjacent and opposite outer surface 20 of the airlaid component 14. In preferred embodiments, the opposing outer surfaces 18, 20 of the fluid distribution and airlaid components 12, 14 are disposed directly opposite each other so that the surfaces of each component are in contact with each other.

Figure 2:
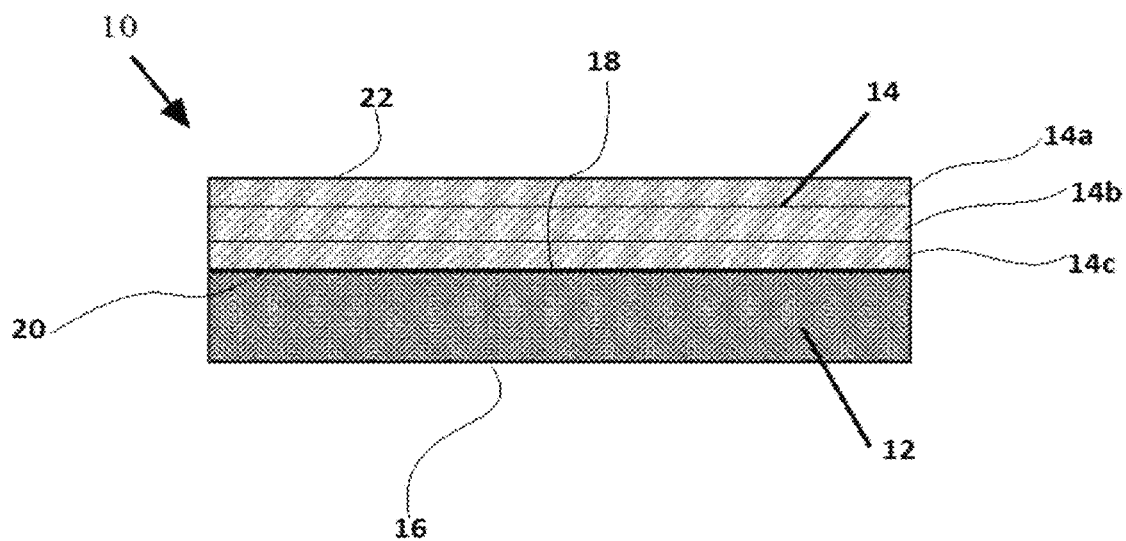
FIG. 2 is a cross-sectional side view of a composite sheet in accordance with at least one embodiment of the present invention in which the composite sheet includes a plurality of airlaid layers.

In some embodiments, the airlaid component 14 may comprise one or more airlaid layers. In this regard, FIG. 2 illustrates an embodiment of the invention in which the airlaid component comprises a plurality of airlaid layers that are formed overlying the fluid acquisition component 12. Preferably, each of the airlaid layers are adjacent to, and in direct contact with, immediately adjacent layers of the airlaid component so that adjacent layers are in fluid communication with respect to each other.

In general, the mass of the fluid acquisition component comprises from about 8 to 85 weight percent of the composite sheet, based on the total weight of the composite sheet. In one embodiment, the mass of the fluid acquisition component comprises from about 20 to 75 weight percent of the composite sheet, and in particular, from about 30 to 60, based on the total weight of the composite sheet.

The mass of the airlaid component comprises from about 15 to 92 weight percent of the composite sheet, based on the total weight of the composite sheet. In one embodiment, the mass of the airlaid component comprises from about 20 to 80 weight percent of the composite sheet, and in particular, from about 30 to 70, based on the total weight of the composite sheet.

Composite sheets in accordance with the present invention are particularly useful as a fluid AQDL component in the manufacture of absorbent articles. Typically, such fluid AQDL components need to balance properties in order to quickly move fluids away from the skin of the wearer, and uniformly distribute them into the absorbent core of the absorbent article. If the fluid is transported to quickly through the AQDL component, the fluid may not distribute laterally (in the x-y directions) through the layer. This may result in too much fluid being localized in one region of the absorbent core. Ideally, it is desirable to have the fluid move quickly through the fluid AQDL component while at the same time, the fluid is distributed laterally through the component. This allows the fluid to be absorbed over a large surface area of the absorbent core.

To achieve this desired balance, it is important that the fluid AQDL component have good fluid absorption properties good wicking properties (capillary action of the fluid moving through the component), low fluid acquisition times (the length of time it takes for a material to absorb a given amount of fluid) as well as good fluid retention properties. The first three properties contribute to how quickly the fluid is moved away from the skin of the wearer and into the absorbent core, and the fluid retention property helps to balance these properties to allow the fluid to be laterally distributed prior to transport into the absorbent core.

As absorbent articles are typically meant to worn by an individual, the comfort of the material to the wearer is also important. If the material is inflexible, stiff, or rigid, the wearer is most likely to reject the absorbent article. Accordingly, it is desirable for the absorbent article to not only provide the balance of the above-described properties, but to also to have resiliency so to provide improved comfort and fit to the wearer.

The inventors of the present invention have found that composite sheets in accordance with the invention provide a good balance of fluid absorption, fluid wicking, fluid acquisition time, and fluid retention, as well as providing a composite sheet having good resiliency. As a result, composite sheets in accordance with embodiments of the invention are particularly useful as a AQDL component in the manufacture of absorbent articles.

In one aspect, composite sheets in accordance with embodiment of the invention are characterized by fluid acquisition times ranging from about 0.75 seconds to about 2 seconds, and in particular, from about 0.8 to 1.5 seconds, and in particular, from about 0.84 to 1.3 seconds.

In one aspect, composite sheets in accordance with embodiment of the invention are characterized by a fluid absorption ranging from about 15 to 30 g/g, and in particular, from about 20 to 26 g/g, and in particular, from about 20 to 25 g/g.

In one aspect, composite sheets in accordance with embodiment of the invention are characterized by a fluid retention ranging from about 8 to 15 g/g, and in particular, from about 9 to 14 g/g, and in particular, from about 10 to 12 g/g.

In one aspect, composite sheets in accordance with embodiment of the invention are characterized by a fluid wicking height ranging from about 10 to 50 mm, and in particular, from about 15 to 45 mm, and more particularly, from about 15 to 40 mm.

In one aspect, composite sheets in accordance with embodiment of the invention are characterized by a resiliency ranging from about 30 to 60%, and in particular, from about 35 to 55%, and more particularly, from about 40 to 50%.

In one embodiment, composite sheets in accordance with the invention may be characterized by a fluid acquisition time ranging from about 0.5 seconds to about 2 seconds; a fluid absorption ranging from about 15 to 30 g/g; a fluid retention ranging from about 8 to 15 g/g; a fluid wicking height ranging from about 10 to 50 mm; and a resiliency ranging from about 30 to 60%. For example, the composite sheet may have a fluid acquisition time ranging from about 0.65 to 1.5 seconds; a fluid absorption ranging from about 20 to 26 g/g; a fluid retention ranging from about 9 to 14 g/g; a fluid wicking height ranging from about 15 to 45 mm; and a resiliency ranging from about 35 to 55%. In certain embodiments, the composite sheet may have a fluid acquisition time ranging from about 0.84 to 1.3 seconds; a fluid absorption ranging from about 20 to 25 g/g; a fluid retention ranging from about 10 to 12 g/g; a fluid wicking height ranging from about 15 to 40 mm; and a resiliency ranging from about 40 to 55%.

In a preferred embodiment, the composite sheet has a fluid acquisition of about 1.25 seconds; a fluid absorption of about 25 g/g; a fluid retention of about 10 g/g; a fluid wicking height of about 40 mm; and a resiliency of about 40%.

The basis weight of the composite sheet may range from about 25 to 400 grams per square meter ($g/m^2$), and in particular, from about 40 to 225 $g/m^2$, and more particularly, from about 50 to 180 $g/m^2$. In a preferred embodiment, the composite sheet has a basis weight that is about 50 to 100 $g/m^2$.

The thickness of the composite sheet may range from about 1 to 6 mm, and in particular, from about 1.3 to 4.5 mm, and more particularly, from about 1.5 to 3.0 mm. In a preferred embodiment, the composite sheet has a thickness that is about 1.6 to 2.5 mm.

Fluid Acquisition Layer

In one embodiment, the fluid acquisition component comprises a fluid acquisition layer comprising a nonwoven fabric having a relatively permeable and porous structure so that a fluid, upon impinging on the surface of the fluid acquisition layer, is quickly transported through the fluid acquisition layer, and into the airlaid component 14. The permeable and porous nature of the fluid acquisition layer may generally be characterized by the density of the layer. For example, the density of the fluid acquisition layer may be from about 0.02 to 0.07 $g/cm^3$, and in particular, from about 0.03 to 0.06 $g/cm^3$. In a preferred embodiment, the density of the fluid acquisition layer is from about 0.04 to 0.05 $g/cm^3$.

A wide variety of different nonwoven fabrics may be used as the fluid acquisition layer. In one embodiment, the nonwoven fabric of the fluid acquisition layer comprises a carded nonwoven fabric comprising staple fibers. Typical lengths of the staple fibers in the fluid acquisition layer may range from about 20 to 100 mm, and in particular, from about 25 to 60 mm, and more particularly, from about 35 to 55 mm.

Other examples of nonwovens that may be used as the fluid acquisition layer may include latex bonded carded fabrics and spunlace nonwovens. The fibers of the fluid acquisition layer may be bonded in a variety of manners including, thermal bonding, resin bonding, stitch bonding, mechanical bonding, such as needle punch or hydroentanglement, and the like.

The staple fibers may comprise monocomponent or multicomponent fibers. In one embodiment, the staple fibers comprise bicomponent fibers have a sheath/core configuration. Examples of bicomponent fibers include side-by-side, islands in the sea, and sheath/core arrangements. Preferably, the fibers have a sheath/core structure in which the sheath comprises a first polymer component, and the core comprises a second polymer component. In this arrangement, the polymers of the first and second polymer components may be the same or different from each other. For example, in one embodiment, the sheath comprises a first polymer component, and the core comprises a second polymer component that is different or the same as the first polymer component. In a preferred embodiment, the first and second polymer components of the bicomponent fibers are different from each other.

In some embodiments the staple fibers of the fluid acquisition layer may have a sheath/core configuration in which the core is centered relative to the sheath. Alternatively, the core may be present in an off-set configuration relative to the sheath. In this configuration, the core not centrally aligned relative to the sheath. As a result, when heat is applied, such as during bonding, the fibers will have a tendency to curl or crimp due, which in turn may help provide loft to the fluid acquisition layer.

In one embodiment, the first polymer component of the sheath comprises a polymer having a lower melting temperature than that of the second polymer component comprising the core. The lower melting polymer of the sheath will promote bonding while the polymer component of the core having a higher melting temperature will provide strength to the fiber and thus to the final bonded nonwoven.

Generally, the weight percentage of the sheath to that of the core in the fibers may vary widely depending upon the desired properties of the nonwoven fabric. For example the weight ratio of the sheath to the core may vary between about 10:90 to 90:10, and in particular from about 20:80 to 80:20. In a preferred embodiment, the weight ratio of the sheath to the core is about 60:40 to 40:60, with a weight ratio of about 50:50 being preferred.

Generally, the fluid acquisition layer has a basis weight ranging from about 18 to 100 (g/m$^2$), and in particular, from about 25 to 80 g/m$^2$, and more particularly, from about 30 to 55 g/m$^2$. In a preferred embodiment, the fluid acquisition layer has a basis weight that is about 35 to 40 g/m$^2$.

The thickness of the fluid acquisition layer may range from about 0.4 to 4 mm, and in particular, from about 0.7 to 3 mm, and more particularly, from about 0.7 to 2 mm. In a preferred embodiment, the fluid acquisition layer has a thickness that is about 0.8 to 1.5 mm.

A wide variety of polymers may be used for preparing staple fibers for use in the fluid acquisition layer. Examples of suitable fibers include may include polyolefins, such as polypropylene and polyethylene, and copolymers thereof, polyesters, such as polyethylene terephthalate (PET), polytrimethylene terephthalate (PTT), and polybutylene terephthalate (PBT), nylons, polystyrenes, copolymers, and blends thereof, and other synthetic polymers that may be used in the preparation of fibers. In one embodiment, the staple fibers have a sheath/core configuration comprising a polyethylene sheath and a polypropylene core. In other embodiments, the staple fibers may have a sheath/core configuration comprising a polyethylene sheath and a polyester core, such as a core comprising polyethylene terephthalate.

In some embodiments, the staple fibers may comprise a blend of fibers such as a blend of bicomponent staple fibers having a polyethylene sheath and a polyethylene terephthalate core, and bicomponent staple fibers having a polyethylene sheath and a polypropylene core. In one embodiment, the fibers of the fluid acquisition layer may include eccentric bicomponent staple fibers having a polyethylene sheath and a polyethylene terephthalate core, a fineness of 4.3 dtex, and an average length of 38 to 51 mm. Examples of such fibers are available from IndoramaPolyester Industries Public Company Limited under the product name TS47.

The above noted polymers are generally considered to be derived from synthetic sources, such as a petroleum derived polymer. In some embodiments, it may be desirable to provide a fluid acquisition layer comprising one or more sustainable polymer components. In contrast to polymers derived from petroleum sources, sustainable polymers are generally derived from a bio-based material. In some embodiments, a sustainable polymer component may also be considered biodegradeable. A special class of biodegradable product made with a bio-based material might be considered as compostable if it can be degraded in a composing environment. The European standard EN 13432, "Proof of Compostability of Plastic Products" may be used to determine if a fabric or film comprised of sustainable content could be classified as compostable.

In one such embodiment, the fluid acquisition layer comprises staple fibers comprising a sustainable polymer component. Preferably, the staple fibers are substantially free of synthetic materials, such as petroleum-based materials and polymers. For example, fibers comprising the fluid acquisition layer may have less than 25 weight percent of materials that are non-bio-based, and more preferably, less than 20 weight percent, less than 15 weight percent, less than 10 weight percent, and even more preferably, less than 5 weight percent of non-bio-based materials, based on the total weight of the fluid acquisition layer.

In one embodiment, sustainable polymers for use may include polylactic acid and bio-based derived polyethylene. Generally, polylactic acid based polymers are prepared from dextrose, a source of sugar, derived from field corn. In North America corn is used since it is the most economical source of plant starch for ultimate conversion to sugar. However, it should be recognized that dextrose can be derived from sources other than corn. Sugar is converted to lactic acid or a lactic acid derivative via fermentation through the use of microorganisms. Thus besides corn other agricultural based sugar source could be used including sugar beets, sugar cane, wheat, cellulosic materials, such as xylose recovered from wood pulping, and the like. Similarly, bio-based polyethylene can be prepared from sugars that are fermented to produce ethanol, which in turn is dehydrated to provide ethylene. A preferred sustainable polymer for use in the present invention comprises polylactic acid (PLA).

In certain embodiments, the sheath and the core both comprise a PLA resin. In these embodiments, a PLA spunbond nonwoven fabric may be provided that is substantially free of synthetic polymer components, such as petroleum-based materials and polymers. For example, the fibers of the PLA spunbond nonwoven fabric may have a bicomponent arrangement in which the both components are PLA based to thus produce a fiber that is 100% PLA. As used herein, "100% PLA" may also include up to 5% additives including additives and/or masterbatches of additives to provide, by way of example only, color, softness, slip, antistatic protection, lubricity, hydrophilicity, liquid repellency, antioxidant protection and the like. In this regard, the nonwoven fabric may comprise 95-100% PLA, such as from 96-100% PLA, 97-100% PLA, 98-100% PLA, 99-100% PLA, etc. When such additives are added as a masterbatch, for instance, the masterbatch carrier may primarily comprise PLA in order to facilitate processing and to maximize sustainable content within the fibers. For example, the PLA staple fibers of the fluid acquisition layer may comprise one or more additional additives. In such embodiments, for instance, the additive may comprise at least one of a colorant, a softening agent, a slip agent, an antistatic agent, a lubricant, a hydrophilic agent, a liquid repellent, an antioxidant, and the like, or any combination thereof.

In one embodiment, the PLA polymer of the sheath may be the same PLA polymer as that of the core. In other embodiments, the PLA polymer of the sheath may be a different PLA polymer than that of the core. For example, the bicomponent fibers may comprise PLA/PLA bicomponent fibers such that the sheath comprises a first PLA grade, the core comprises a second PLA grade, and the first PLA grade and the second PLA grade are different (e.g., the first PLA grade has a lower melting point than the second PLA grade). By way of example only, the first PLA grade may comprise up to about 5% crystallinity, and the second PLA grade may comprise from about 40% to about 50% crystallinity.

In some embodiments, for instance, the first PLA grade may comprise a melting point from about 125° C. to about 135° C., and the second PLA grade may comprise a melting point from about 155° C. to about 170° C. In further embodiments, for example, the first PLA grade may comprise a weight percent of D isomer from about 4 wt. % to about 10 wt. %, and the second PLA grade may comprise a weight percent of D isomer of about 2 wt. %.

For example, in one embodiment, the core may comprise a PLA having a lower % D isomer of polylactic acid than that of the % D isomer PLA polymer used in the sheath. The PLA polymer with lower % D isomer will show higher degree of stress induced crystallization during spinning while the PLA polymer with higher D % isomer will retain a more amorphous state during spinning. The more amorphous sheath will promote bonding while the core showing a higher degree of crystallization will provide strength to the fiber and thus to the final bonded web. In one particular embodiment, the Nature Works PLA Grade PLA 6752 with 4% D Isomer can be used as the sheath while NatureWorks Grade 6202 with 2% D Isomer can be used as the core.

In some embodiments, the sheath may comprise a bio-based polyethylene, and the core may comprise a PLA polymer.

In some embodiments, the sheath may comprise a PLA polymer and the core a synthetic polymer, such as polypropylene.

Airlaid Layer

The airlaid component 14 includes at least one airlaid layer comprising a blend of cellulose staple fibers and non-cellulose staple fibers. As discussed in greater detail below, the at least one airlaid layer is deposited onto a surface of the fluid distribution component, and the resulting composite sheet material is then through air bonded to form a coherent composite structures in which the staple fibers of both the fluid acquisition layer and the airlaid layer are bonded to each other.

During the process of making the composite sheet material, a mixture of cellulose staple fibers and non-cellulose staple fibers are first mixed in an air stream, and then deposited onto a surface of the fluid acquisition layer. Thereafter, the fibers of the fluid acquisition layer and airlaid layer are bonded to each other by introducing a stream of heated gas, such as air, through the composite sheet material. For example, in one embodiment the composite sheet material is passed through an oven that it heated to a temperature that is above the softening temperature of the non-cellulose staple fibers, which causes the low-melt sheath polymer component of the staple fibers to at least partially soften and flow so that upon cooling the fibers fuse and bond to adjacent cellulose and non-cellulose fibers.

A wide variety of different cellulose materials may be used for the cellulose fibers. For example, digested cellulose fibers from softwood (derived from coniferous trees), hardwood (derived from deciduous trees) or cotton linters can be utilized. Fibers from Esparto grass, bagasse, kemp, flax, and other lignaceous and cellulose fiber sources may also be utilized. Other fibers include absorbent natural fibers made from regenerated cellulose, polysaccharides or other absorbent fiber-forming compositions. For reasons of cost, ease of manufacture and disposability, preferred fibers are those derived from wood pulp (e.g., cellulose fibers). In particular, examples of suitable materials include treated and untreated pulp, including pulps of hardwood, softwood, straw, chemical pulp, fluff pulp, chemi-mechanical pulp, thermal mechanical pulp, and mixtures thereof. Suitable cellulose fibers may be obtained from Weyerhauser under the product designations NB416 and NB 405, International Paper Super soft M, Georgia Pacific under the product designations 4821, 4822, and 4823, and mixtures thereof.

The cellulose fibers generally have a fiber length that is about 0.8 to 10 mm, and in particular, from about 2 to 8 mm, and more particularly, from about 2 to 5 mm.

Suitable materials for the non-cellulose staple fibers for use in the airlaid layer may comprise monocomponent or multicomponent fibers, or mixtures of moncomponent and multicomponent fibers. In a preferred embodiment, the non-cellulose staple fibers of the airlaid layer comprise bicomponent fibers having a sheath/core configuration.

Examples of polymers that may be used to prepare the non-cellulose fibers include those discussed above for use in the fluid acquisition layer. For example, the non-cellulose fibers may comprise sustainable polymers, such as PLA and bio-based polyethylene, synthetic fibers, and combinations thereof. In one embodiment, the non-cellulose staple fibers may comprise a sheath comprising a bio-based polyethylene, and a core comprising a PLA polymer. In other embodiments, the non-cellulose staple fibers may comprise a PLA polymer sheath and a PLA polymer core, wherein the PLA polymers may be the same or different from each other.

In other embodiments, the sheath may comprise a PLA polymer and the core a synthetic polymer, such as polypropylene.

In one embodiment, the non-cellulose staple fibers may comprise bicomponent staple fibers having a polyethylene sheath and a polyethylene terephthalate core. One such example is bicomponent staple fiber having a fineness of 2.2 dtex, and an average length of 3 mm, which are available from Toray Chemical Korea Inc. under the product name EZBON A (UN-204). A further example is an eccentric bicomponent staple fibers having a polyethylene sheath and a polyethylene terephthalate core. Such a fiber is available from IndoramaPolyester Industries Public Company Limited under the product name TS47 (a fineness of 4.3 dtex, and an average length of 3 mm). Another example is a bicomponent staple fibers having a polyethylene sheath and a polyethylene terephthalate core is available from Trevira under the product designation T255 staple fibers. These staple fibers have a fineness of 4.3 dtex, and an average length of 3 mm.

In another embodiment, the non-cellulose staple fibers may comprise bicomponent staple fibers having a polyethylene sheath and a polypropylene core. One such example is a staple fiber having a fineness of 4.0 dtex, and an average length of 40 mm, which are available from Yangzhou Petrochemical Co. Ltd. under the product name Y116. Another example of bicomponent staple fibers having a polyethylene sheath and a polypropylene core, a denier of 6.0, and an average length of 51 mm, are available from JiangNan High Polymer Fiber under the product designation JNGX-PZ11-6*51L.

In some embodiments, the non-cellulose fibers may comprise blends of fibers, such as blends comprising bicomponent PE/PET and PE/PP staple fibers.

The non-cellulose staple fibers typically have lengths ranging from about 3 to 15 mm, and in particular, from about 3 to 10 mm, and more particularly, from about 3 to 6 mm.

Collectively, the basis weight of the airlaid layer(s) may range from about 7 to 300 g/m², and in particular, from about 20 to 200 g/m², and more particularly, from about 30 to 100 g/m². In a preferred embodiment, the airlaid layer has a basis weight that is about 50 g/m².

In some embodiments, one or more of the airlaid layers may include a super absorbent polymer or super absorbent fibers that are mixed with the cellulose and non-cellulose fibers. The super absorbent polymer or super absorbent fibers may be present in only one layer of the air laid component or present in multiple airlaid layers of the airlaid component. When present, the super absorbent polymer or super absorbent fibers may be present in an amount from about 10 to 50 weight percent, and in particular, from about 10 to 35 weight percent, based on the total weight of the air laid layer in which the super absorbent polymer or super absorbent fibers are present.

Additional Layers

Figure 3:
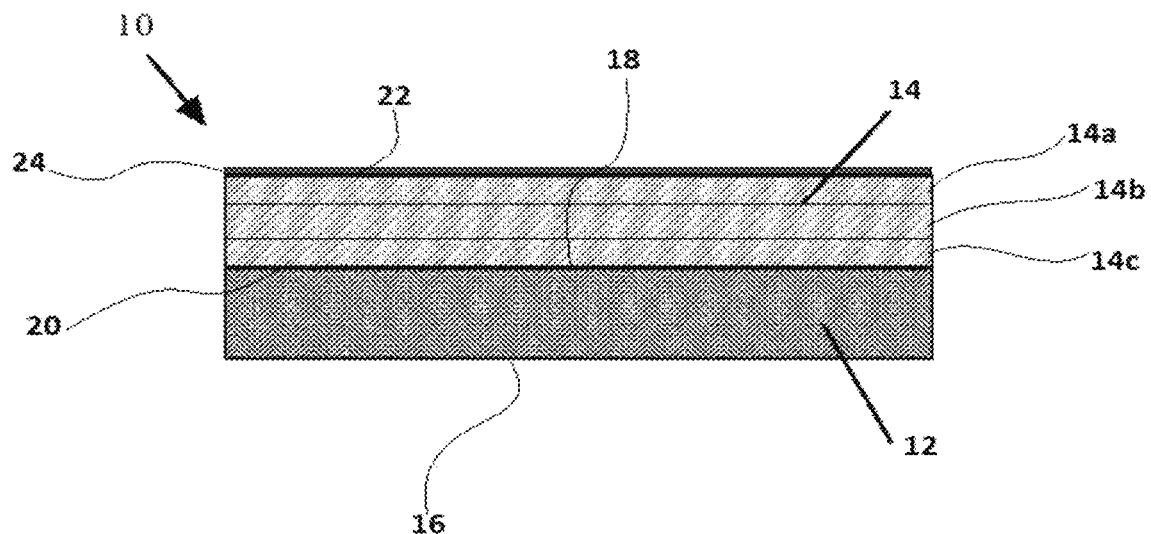
FIG. 3 is a cross-sectional side view of a composite sheet in accordance with at least one embodiment of the present invention in which the composite sheet includes a coating layer deposited on the surface of the outermost airlaid layer.

In some embodiments, the composite sheet may further comprise a polymer-based layer that is deposited on the outer surface 22 of the airlaid component. In this regard, FIG. 3 illustrates an embodiment of the invention in which the composite sheet material 10 comprises a coating layer 24 disposed on the outer surface of the airlaid component 14. In one embodiment, the coating layer may be applied a composition comprising a carrier, such as water or an organic solvent, and a polymeric material dispersed in the carrier. For example, in one embodiment, the coating layer may comprise a latex formulation of an aqueous polymer dispersion comprising ethylene vinyl acetate, acrylates, polyacrylates, phenylethylenes, butadienes, styrene butadiene-acrylic acids, polyvinyl alcohols, and mixtures thereof.

In one embodiment, the latex formulation comprises a polymer produced from the monomers vinyl acetate and ethylene, which is available from Wacker under the product name VINNAPAS® 192, with a solid constituent ranging from 50 to 55%.

The coating layer may be applied to the composite sheet material in variety of different ways, such as, spray coating, foam coating, kiss coating, and the like.

In the case of an aqueous dispersion or emulsion, the coating layer is applied as a liquid, which may then be cured and dried to form a solid coating adhered to the composite sheet. The amount of the coating layer added to the composite sheet, following any drying and cure step is typically from about 1 to 5 weight percent, and in particular, from about 1.5 to 3 weight percent, and more particularly, from about 1.75 to 2.25 weight percent, based on the total weight of the composite sheet.

Process of Preparing the Composite Sheet.

Figure 4A:
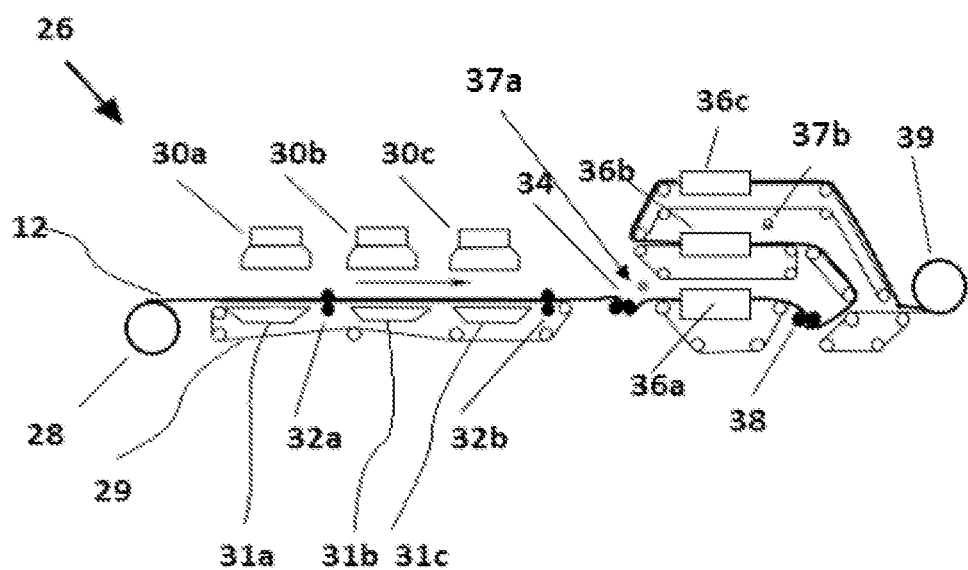
FIG. 4A is a schematic illustration of a system for preparing a composite sheet in accordance with an embodiment of the present invention.

With reference to FIG. 4A, a system and associated process for preparing the composite sheet material is shown and designated with reference character 26. The system 26 includes a source of fabric for use as the fluid acquisition layer 12. In the illustrated embodiment, the source is shown as a spool 28 on which the previously formed fluid acquisition layers if wound. However, it should be recognized that the system may include a fabric forming device, for example, a card or spinning beam, for preparing the nonwoven fabric of the fluid acquisition layer in a continuous line with respect to the rest of the system 26.

As shown, the nonwoven fabric of the fluid acquisition layer 12 is removed from the spool 28 and deposited on a collection surface 29, such as an endless belt. The fluid acquisition layer is then transported to a series of airlaid fabric forming heads (30a, 30b, 30c). At each forming head a stream of cellulose and non-cellulose staple fibers are homogeneously mixed to form a stream of mixed staple fibers. Each forming head then deposits the mixed stream of staple fibers onto the surface of the fluid acquisition layer 12. A vacuum 31a, 31b, 31c, is positioned underneath the collection surface, and below each of the forming heads to assist in depositing the mixed stream of fibers onto the fluid acquisition layer 12. The system may optionally include one or more pairs of compaction rollers 32a, 32b that are disposed following each forming head. When present, compaction rollers 32a, 32b may be heated. For example, the compaction rollers 32a, 32b may be heated at a temperature ranging from about 90 to 110° C.

Although three airlaid forming heads are shown, it should be understood that the system may include any number of forming heads depending on the desired number of airlaid layers that are deposited onto the fluid acquisition layer 12. For example, the number of airlaid forming heads may range from 1 to 10, such as 2 to 8, 3 to 6, and 4 to 5. It should also be recognized that during operation of the system, one or more of the forming heads may not be used.

Figure 4B:
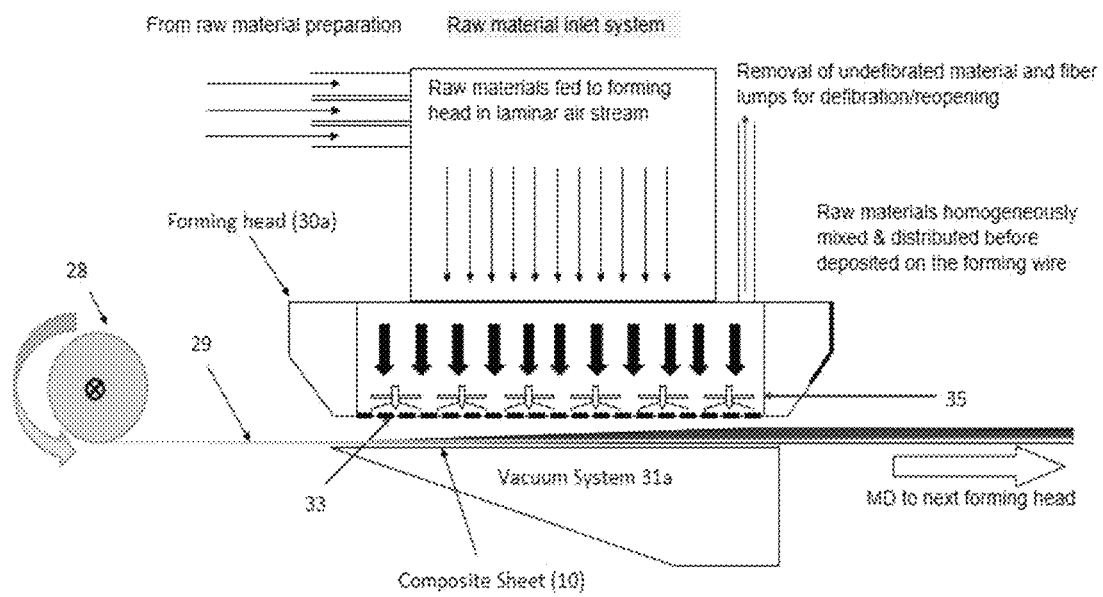
FIG. 4B shows a schematic illustration of a forming head for preparing an airlaid layer in accordance with at least one embodiment of the present invention.

With reference to FIG. 4B, a forming head that may be used in certain embodiments of the invention is illustrated. As can be seen, the forming head 30a includes a plurality of agitators 35 that create a turbulent flow within the forming head. The turbulent flow causes the cellulose and non-cellulose staple fibers to mix and form a homogenous mixture. The forming head also includes a screen 33 that limits/controls the output of the staple fibers from the forming head and thereby helps to form an evenly distributed airlaid layer.

Turning back to FIG. 4A, the composite sheet material with the thus deposited airlaid layers is transported to a first heating oven 36a. The first heating oven is typically maintained at a temperature that is sufficient to soften and melt the non-cellulose fibers of the airlaid layers. This melting causes the polymers to flow and fuse to adjacent fibers to provide a coherent composite sheet. For example, in embodiments in which the non-cellulose staple fibers comprised a bicomponent fiber having a polyethylene sheath, the composite sheet material may be heated to a temperature above the melting point of the sheath, but below the melting point of the core. For polyethylene, the temperature of the oven will typically be from about 120 to 150° C.

In some embodiments, the system may include one or more embossing rolls 34 that may be used to impart an embossed pattern on the surface of the composite sheet. In some embodiments, the system may also include a pair of calibration rolls 38 to adjust the thickness of the composite sheet, and/or assist in interlayer bonding between adjacent layers. Calibration roll 38 may be define a nip or be gapped. In some embodiments, the calibration roll is heated; in other embodiments, the calibration roll is not heated.

Prior to this initial thermal bonding in the first heating oven, the composite sheet is transported to an application station 37a at which point a coating layer may be applied to the surface of the outermost airlaid layer. This coating layer may be applied using conventional techniques such as are known in the art including, spray coating, kiss roll application, and the like. In a preferred embodiment, a coating of an aqueous latex dispersion is applied to the surface of the composite web. In some embodiments, a second application coating layer may be applied to the opposite side of the coating via application station 37b.

Following application of the optional second coating layer, or any other materials to the surface of the composite sheet, the composite sheet is transported to a second heating oven 36b that is maintained at a temperature that dries and cures the previously applied coating layers. Optionally, the composite sheet material may be further heated in a third oven 36c.

The bonded and dried composite sheet material may then be wound onto roll 39. In some embodiments, the composite sheet may be cut continuously in the machine direction to form a plurality of individual composite sheets that are each wound onto separate rolls.

Figure 5:
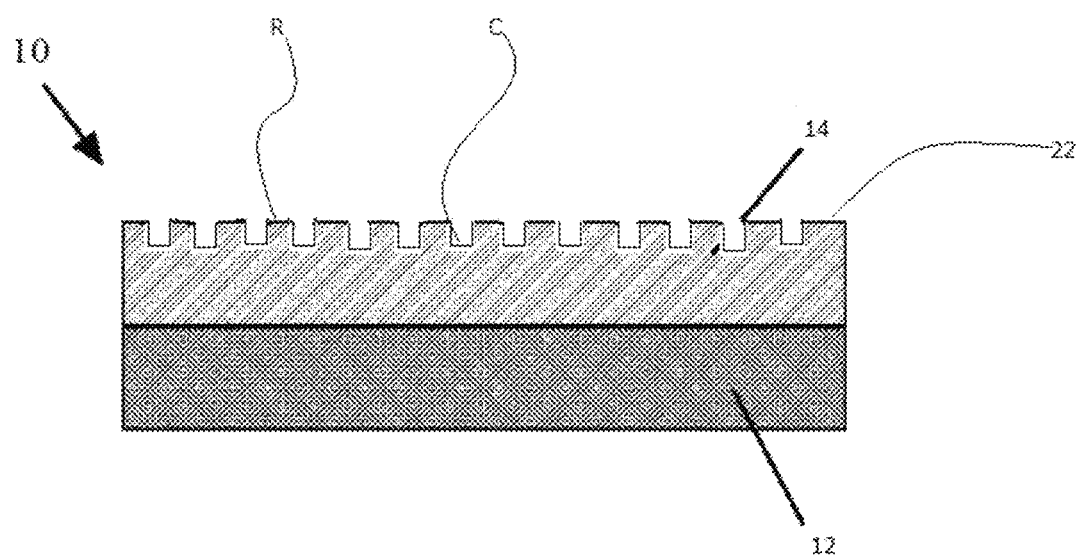
FIG. 5 is a cross-sectional side view of a composite sheet in accordance with at least one embodiment of the present invention in which the composite sheet includes a plurality of alternating ridges and channels formed on the surface of the outermost airlaid layer.

In some embodiments, it may be desirable to emboss a pattern onto the airlaid component of the composite sheet. For example, using the embossing roll 34 shown in FIG. 4A. In this regard, FIG. 5 shows an embodiment of the invention in which the surface 22 of the composite sheet 10 has a plurality of alternating ridges R and channels/grooves C that are defined on the surface of the outermost airlaid layer. In the construction of an absorbent article, the fluid acquisition layer is typically disposed towards the top sheet whereas the airlaid component is disposed towards the absorbent core. Fluid entering the composite sheet material is distributed through the fluid acquisition layer and into the airlaid layer(s). As it is transported towards the absorbent core, the plurality of ridges and channels helps to further distribute the fluid so that it may be more evenly distributed throughout the airlaid layer, and hence, throughout the absorbent core.

The pattern of alternating ridges and channels typically extend in the machine direction of the composite sheet material, but other orientations are possible, such as diagonally or in the cross direction, or in a nonlinear, such as serpentine, and/or noncontinuous configuration.

The pattern may be produced by a roll in which having a pattern of alternating raised surfaces and grooves that extend circumferentially about the roll. In some embodiments, the roll may be heated and pressure may be applied to the surface of the composite sheet material to help facilitate formation of the pattern of alternating grooves and ridges. The widths of each groove (e.g., distance between adjacent ridges) may vary depending upon the intended application of the absorbent article, but will typically range from about 0.2 to 10 mm, and in particular, from about 1 to 6 mm, and more particularly, from about 2 to 3 mm. The depth of each groove will typically be about 0.1 to 5 mm, and in particular, from about 0.3 to 3 mm.

Figure 6:
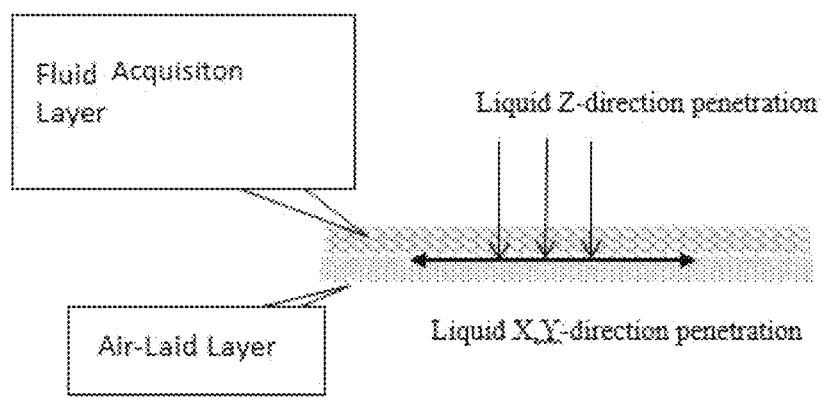
FIG. 6 depicts fluid transport and distribution through a composite sheet material.

As discussed previously, the composite sheet material of the present invention is particularly useful as an AQDL component in absorbent articles. In particular, the composite sheet is able to rapidly transport fluids through the fluid acquisition layer and then distribute the fluid laterally through the one or more airlaid layers. This transport of fluid is illustrated in FIG. 6.

Absorbent Articles

Composite sheets in accordance with the present invention may be used in a wide variety of different articles, and in particular, a wide variety of absorbent articles.

Figure 7:
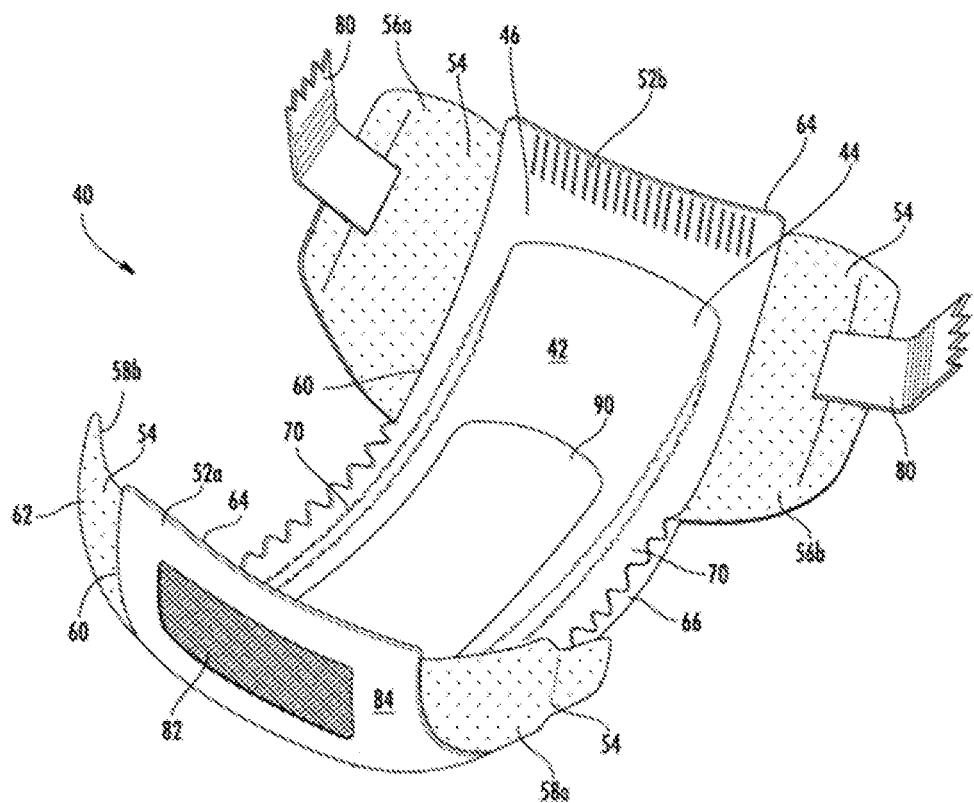
FIG. 7 is an illustration of an absorbent article in accordance with at least one embodiment of the present invention.

With reference to FIG. 7, an embodiment of an absorbent article ("diaper") in accordance with embodiments of the present invention is shown and broadly designated by reference number 40. The diaper 40 includes a core region 42 in which an absorbent core 44 is disposed. A chassis region 46 surrounds the core region 42, and includes a front 48, back 50, and front and back waist regions 52a, 52b. The chassis region comprised of front, back and core regions generally has a composite structure comprising a liquid permeable topsheet and a liquid impermeable backsheet that are attached to each other along opposing surfaces to define a cavity there between in which the absorbent core is disposed.

Suitable materials for the topsheet, backsheet, and absorbent core may generally comprise any materials conventionally used in the manufacture of absorbent articles.

As shown in FIG. 7, the diaper also includes a composite sheet material 10 in accordance with at least one embodiment of the present invention. The composite sheet 10 defines a fluid acquisition distribution system 90 (i.e., AQDL component) of the absorbent article. As discussed above, the composite sheet 10 defines a fluid distribution/acquisition component that helps to efficiently facilitate transfer of fluid from the wearer to the absorbent core 44.

In some embodiments, the front and back regions of the diaper also each includes a pair of ears 54 that are disposed in the waist regions of the diaper. (As used herein, the term "disposed" is used to mean that an element(s) of the diaper is formed (joined and positioned) in a particular place or position as a unitary structure with other elements of the diaper or as a separate element joined to another element of the diaper.) The ears 54 provide an elastically extensible feature that provides a more comfortable and contouring fit by initially conformably fitting the diaper to the wearer and sustaining this fit throughout the time of wear well past when the diaper has been loaded with exudates since the elasticized side panels allow the sides of the diaper to expand and contract.

In addition, the ears 54 develop and maintain wearing forces (tensions) that enhance the tensions developed and maintained by a fastening system, discussed in greater detail below, to maintain the diaper 40 on the wearer and enhance the waist fit. As shown in FIG. 7, the diaper includes a pair of back ears 56a, 56b which are joined to the back region 50 of the diaper chassis proximate to the back waist region 52b, and a pair of front ears 58a, 58b, which are joined to the front region 48 of the diaper chassis proximate of the front waist region 52a.

The front and back ears may be joined to the chassis region 46 by any bonding method known in the art such as adhesive bonding, pressure bonding, heat bonding, and the like. In other embodiments, the front and/or back ears may comprise a discrete element joined to the chassis region with the chassis region 46 having a layer, element, or substrate that extends over the front and/or back ear. For example, each ear may comprise a portion of the diaper chassis region that extends laterally outwardly from and along the side edge 60 of the chassis region to a longitudinal edge 62 of the diaper 40. In one embodiment, the ears generally extend longitudinally from the end edge 64 of the diaper 40 to the portion of the longitudinal edge 62 of the diaper 20 that forms the leg opening (this segment of the longitudinal edge 62 being designated as leg edge 66). In some embodiments, the ears may comprise a separate fabric or web that has been joined to the topsheet or the backsheet. In other embodiments, each ear may be formed by the portions of the topsheet and the backsheet that extend beyond the side edges of the absorbent core 44.

In one embodiment, the diaper 40 may also include elastic leg cuffs 70 for providing improved containment of fluids and other body exudates. Each elasticized leg cuff 70 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 entitled "Contractable Side Portions for a Disposable Diaper" issued to Buell on Jan. 14, 1975, describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz and Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinent garment having side-edge-leakage-guard gutters configured to contain free liquids within the garment. Each of these patents are incorporated herein by reference. U.S. Pat. No. 6,476,289 entitled "Garment Having Elastomeric Laminate" describes various elastic leg cuff configurations that may also be used in embodiments of the present invention.

In a preferred embodiment, the leg cuffs may comprises a fabric layer having an SMS structure comprising a plurality of elastic strands that are incorporated into the leg cuff structure. Preferably, the leg cuffs comprises a material having liquid barrier properties.

One example of a fabric for use in forming leg cuffs comprises an SMS fabric having a spunbond nonwoven layer comprising bicomponent fibers having a first polymer component sheath and a second polymer component core. Examples of materials for the sheath and core include polyolefins, such as polypropylene and polyethylene, polyesters, PLA based polymers, and the like. In one embodiment, the bicomponent fibers comprise a polypropylene sheath, and a PLA core. An example of a polypropylene material for use in this embodiment may have a melt flow rate (MFR) between 20 to 40 g/10 min (measured in accordance with ASTM D1238 (190° C./2.16 kg)) such as, for example, provided by Total Petrochemicals and Refining USA, Inc. of La Port, TX, 77571 USA as grades M 3766 (metallocene polypropylene) and 3764 or 3866 (Zeigler Natta polypropylene). A suitable material for use as the PLA core is available from Nature Works PLA as Grade 6202 with 2% D Isomer. The meltblown layer may comprise a polypropylene having an MFR of 1,300 g/10 min (measured in accordance with ASTM D1238 (190° C./2.16 kg)) such as, for example, provided by Total Petrochemicals and Refining USA, Inc. of La Port, TX, 77571 USA as grade 3962.

In a second example, the leg cuffs may comprise an SMS fabric having a spunbond nonwoven layer comprising bicomponent fibers having a PLA sheath and a PLA core, and a meltblown layer comprising PLA fibers. An example of a suitable PLA material for use as the sheath is PLA grade 6752 with 4% D Isomer, and an example of a suitable PLA material for use as the core is PLA grade 6202 with 2% D Isomer, both of which are available from NatureWorks. A suitable material for the PLA meltblown fibers is PLA grade 6252, which is also available from NatureWorks.

In a third embodiment, the leg cuffs may comprise a fabric having an SMS structure in which the spunbond nonwoven layers comprise a bicomponent fabric having a polypropylene sheath and a PLA core. Examples of suitable materials for the sheath and core are described above. The meltblown layer may comprise meltblown fibers comprising a blend of PLA and polypropylene that has been reclaimed from spunbond bicomponent fibers comprised of PP/PLA using the process taught in International Application PCT/US 2015/012658.

In a fourth embodiment, the leg cuffs may comprise a fabric having an SMS structure in which the spunbond nonwoven layers comprise a bicomponent fabric having a PLA sheath and a PLA core. Examples of suitable materials for the sheath and core are described above. As in the third embodiment discussed above, the meltblown layer may comprise meltblown fibers comprising a blend of PLA and polypropylene that has been reclaimed from spunbond bicomponent fibers comprised of PP/PLA using the process taught in International Application No. PCT/US2015/012658.

Preferably, spunbond fabrics for forming the leg cuffs have a sheath/core ratio of approximately 30/70 to 70/30. In one embodiment, the basis weight of the SMS fabric is between about 8 g/m² and 15 g/m². Preferably, the meltblown content comprises about 10 to 30 weight %, based on the total weight of the SMS fabric. In some embodiments, the SMS fabric for use in forming the leg cuffs has a hydrohead value of greater than about 50 mm as measured in accordance with INDA Test Method WSP 80.6.

In some embodiments, the diaper 40 may also include elastic elements that are disposed around one or more of the waist region 52 and the elastic cuffs. For example, the diaper may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595; 4,710,189; 5,151,092; and 5,221,274.

In some embodiments, the elastic features may comprise elastic elements comprising elastic strands or threads that are contractably affixed between the topsheet and backsheet of the diaper. Such strands or threads can be comprised of a bio-based material, such as natural rubber. As noted above the natural rubber strands are covered by nonwoven, such as the topsheet and/or backsheet to insure elastic component does not directly contact the wearer's skin.

The absorbent article may include a fastening system. The fastening system can be used to provide lateral tensions about the circumference of the absorbent article to hold the absorbent article on the wearer as is typical for taped diapers. This fastening system is not necessary for pull on style of absorbent articles, such as training pants or adult incontinence absorbent articles, since the waist region of these articles is already bonded.

The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. When fastened, the fastening system interconnects the front waist region 52a and the back waist region 52b. When fastened, the diaper 44 contains a circumscribing waist opening and two circumscribing leg openings.

The fastening system may comprise an engaging member 80 and a receiving member 82 (also referred to as a landing zone). The engaging member 80 may comprise hooks, loops, an adhesive, a cohesive, a tab, or other fastening mechanism. The receiving member 82 may comprise hooks, loops, a slot, an adhesive, a cohesive, or other fastening mechanism that can receive the engaging member 80. Suitable engaging member 80 and receiving member 82 combinations are well known in the art and include but are not limited to hooks/loop, hooks/hooks, adhesive/polymeric film, cohesive/cohesive, adhesive/adhesive, tab/slot, and button/button hole. Suitably, the fastening system may comprise a polymer derived from a bio-based material.

In this regard, FIG. 7 further shows a fastening system in which the engaging member comprises a pair of tabs 80 that are joined to the back ears 56a, 56b, and an associated landing zone 82 disposed on a front surface 84 of the diaper 40. In some embodiments, the tabs may include a pressure sensitive adhesive for adhesively attaching the tabs to the landing zone.

Some exemplary surface fastening systems are disclosed in U.S. Pat. Nos. 3,848,594; 4,662,875; 4,846,815; 4,894,060; 4,946,527; 5,151,092; and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; and 5,591,152.

In a preferred embodiment, the fastening system can employ a hook and loop as described in U.S. Pat. No. 9,084,701. In a preferred embodiment, the hook and loop fastening system comprises a female fastening material made of fibrous material and a male fastening material with hooks configured for the fibrous material.

In one embodiment, the female loop material comprises bonded bicomponent fibers comprising a bio-based material, such as spunbond bicomponent fibers having a PLA, and a sheath comprising a sugar cane derived polyethylene polymer. Examples of such materials are described above. An example of a suitable PLA polymer for the core in is available from NatureWorks as PLA Grade 6202.

A second fiber for use as the female loop component providing 50 bio-based material content comprises a sheath of petroleum based polypropylene polymer and a PLA core derived from NatureWorks under the product name PLA Grade 6202. Preferred polypropylenes for use in this embodiment will typically have a melt flow rate (MFR) between 20 to 40 g/10 min (measured in accordance with ASTM D1238 (190° C./2.16 kg)) such as for example provided by Total Petrochemicals and Refining USA, Inc. of La Port, TX, 77571 USA as grades M 3766 (metallocene polypropylene) and 3764 or 3866 (Zeigler Natta polypropylene).

A further example of fibers for constructing a female loop material, providing 50% bio-based material content, comprise spunbond bicomponent fibers in which the core comprises a lignin based polymer and a sheath comprising a petroleum based polyethylene. Such fibers are disclosed as examples 4, 5, 6, 7, 8, and 9 in European Patent No. EP 2,630,285 B1 and U.S. Patent Publication No. 2014/0087618.

Substitution of the petroleum based polyethylene sheath in these examples with a sheath comprised of either the sugar cane derived polyethylene available from Braskem S.A. or the corn derived PLA available from NatureWorks, both polymers disclosed above, would provide fibers having up to a 100% bio-based material content.

A further example of a fiber that can be used for constructing the female loop material is a bicomponent fiber having a core of (PLA), and a sheath comprising PLA. For example, in one embodiment, the core may comprise a PLA having a lower % D isomer of polylactic acid than that of the % D isomer PLA polymer used in the sheath. The PLA polymer with lower % D isomer will show higher degree of stress induced crystallization during spinning while the PLA polymer with higher D % isomer will retain a more amorphous state during spinning. The more amorphous sheath will promote bonding will the core showing a higher degree of crystallization will provide straight to the fiber and thus to the final bonded web.

In one particular embodiment, the Nature Works PLA Grade PLA 6752 with 4% D Isomer can be used as the sheath while NatureWorks Grade 6202 with 2% D Isomer can be used as the core.

A further example of fibers for use in the female loop material, providing at least 50% bio-based material content may comprise a 50/50 blend of cotton fibers and a petroleum based polymer, such as polypropylene. Examples of polypropylene staple fibers useful to form such fabrics are available from Fibervisions Corporation as Grade T-198. Examples of cotton fibers for use to form such nonwoven fabrics include fibers sold under the product name TRUE-COTTON® available from TJ Beall Company, and fibers sold under the product name HIGH-Q ULTRA® available from Barnhardt Manufacturing Company.

The male hooks use in this fastening stem for the preferred embodiment are also comprised of significant sustainable content. The male fastening material including the hooks can be made by casting, molding, profile extrusion, or microreplications where the polymer used is corn derived PLA such as is available from NatureWorks. NatureWorks provides a selection of grades for injection molding that could be used to make such hooks including Grades 3001D, 3052D, 3100HP and 3251D.

Figure 8:
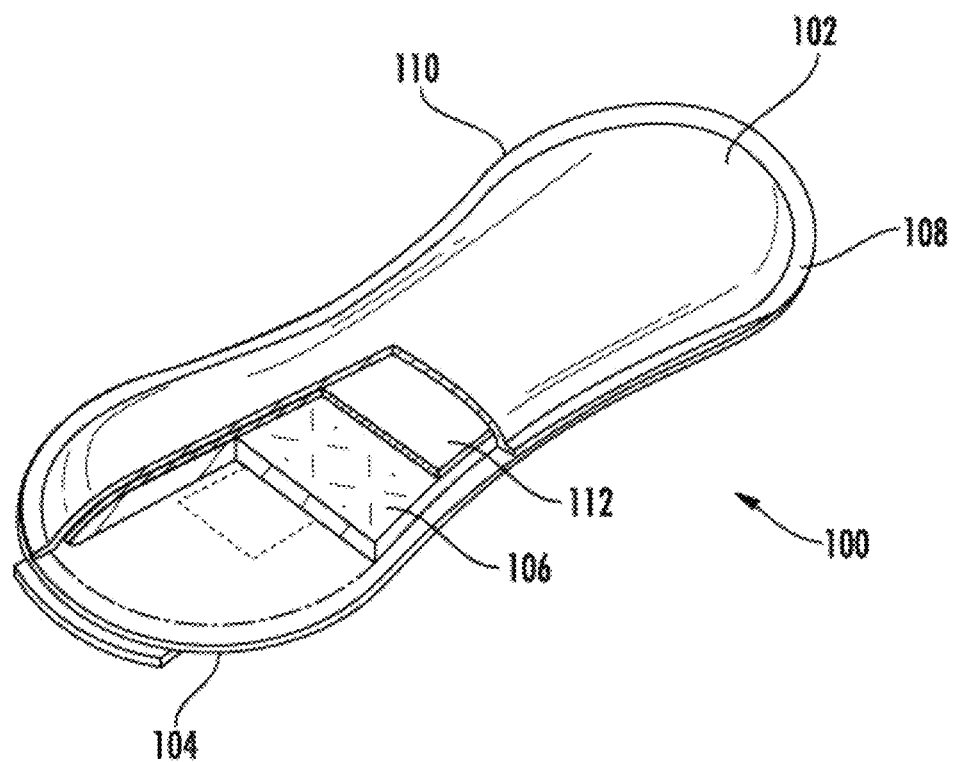
FIG. 8 is an illustration of an absorbent article in accordance with at least one embodiment of the present invention in which the absorbent article is in the form of a feminine sanitary pad.

With reference to FIG. 8, a further embodiment of an absorbent article in accordance with an embodiment of the present invention is illustrated in which the absorbent article is in the form of a feminine sanitary pad, broadly designated by reference character 100.

Pad 100 may include a topsheet 102, backsheet 104, and an absorbent core 106 disposed there between. Preferably, topsheet 102 and backsheet 104 are joined to each other about along opposing outer edges to define a continuous seam 108 that extends about the periphery 110 of the pad 100. Continuous seam 108 may comprise a heat seal that is formed from thermally bonding the topsheet and backsheet to each other. In other embodiments, continuous seam 108 is formed by adhesively bonding the topsheet and backsheet to each other.

Suitable materials for the topsheet, backsheet, and absorbent core may comprise materials typically used in the construction of absorbent articles.

As shown, pad 100 includes a composite sheet 10 defining a fluid AQDL component 112. The AQDL component is disposed between the absorbent core 106 and the topsheet 102. As discussed above, the composite sheet defining the fluid distribution/acquisition component comprises a fluid acquisition layer comprising a carded nonwoven and at least one airlaid layer comprising a blend of cellulose staple fibers and non-cellulose fibers, in which the fibers of the layers are thermally bonded to each other.

Various components of the absorbent article are typically joined via thermal or adhesive bonding. Examples of suitable adhesives include polyethylene, polypropylene, or ethylene vinyl acetate based melt adhesives. In some embodiments, the adhesive may comprise a bio-based adhesive. An example of a bio-based adhesive is a pressure sensitive adhesive available from Danimer Scientific under the product code 92721.

In yet another aspect, certain embodiments of the invention provide absorbent articles. In accordance with certain embodiments, the absorbent article may include a composite sheet in accordance with the present invention In this regard, composite sheets prepared in accordance with embodiments of the invention may be used in wide variety of articles and applications. For instance, embodiments of the invention may be used for personal care applications, for example products for babycare (diapers, wipes), for femcare (pads, sanitary towels, tampons), for adult care (incontinence products), or for cosmetic applications (pads).

EXAMPLES

The following examples are provided for illustrating one or more embodiments of the present invention and should not be construed as limiting the invention.

Unless otherwise defined, the technical terms used in the following embodiments have the same meaning as commonly understood by those skilled in the art to which this invention pertains. The test reagents used in the following embodiments, unless otherwise specified, are conventional reagents; the said experimental methods, unless otherwise specified, are conventional methods.

Test Methods

Thickness was determined in accordance with EDANA 30.5-99 using a digital thickness tester. In accordance with this test, a sample of material is positioned between two plates under a pressure (0.5 kPa), and the distance between the two plates is reported in units of "mm."

Carry out sample taking and cutting according to different product requirements, the size edge of sample to be tested to the edge of the upper side of the instrument should not be less than 5 mm; the sample should be acclimated for at least 4 hours under constant temperature and humidity condition (23±2° C.; relative Humidity: 50%±5%). If acclimation of the sample will not be carried out, the temperature and humidity at that moment should be recorded while performing measurement, only for reference of comparison.

Compression and Resilience:

After taking samples from the aged products without 4 hours of acclimation, complete the first test within 30 minutes, the thickness is T1; after keeping the sample for 4 hours, measure the thickness again, the thickness value is T2, the rebound resilience is expressed by the percentage of (T2−T1/T1).

Test thickness under different pressure by measuring same area of material continuously to simulate the 'human' touch/press process.

Caliper under 0.5 kPa: T1
Caliper under 2.1 kPa: T2
Caliper under 0.5 kPa: T3
% Compression=(T2-T1)/T2×100%
% Resiliency=(T3-T2)/T2×100%

Basis Weight

Basis weight was measured in accordance with EDANA 40.3-90.

Mass determination: the mass of unit area is the mass determination of the sample (gram weight), with unit of $g/m^2$.

Tester: electronic balance (accuracy to 0.001 gram), screens are set around the balance to prevent air flow and other interference factors from impacting the balance.

The samples are required to balance for at least 4 hours under constant temperature and humidity condition (23±2° C.; relative Humidity: 50%±5%). If the balance will not be carried out for the on-line real-time test, the temperature and humidity at that moment should be recorded while performing measurement, only for reference of comparison.

Place the sample to be tested on the balance, after the reading of the balance becomes stable, record the weight in units of grams.

Mass determination (GSM)=A/B

Where: GSM: the determined mass of a sample;
A: weight of a sample;
B: area of a sample.

Tensile strength and elongation at break were measured in accordance with EDANA 20.2-89.

Tensile strength: the tension required to pull a sample with specified size to break at constant speed. The percentage of the length when the sample is pulled to break to the original length of the sample is the elongation at breaking, in unit of "%".

Tester: Zwick 2.5 strength tester

Cut the sample to a size of 200 mm×25.4 mm, the sample is required to acclimate for at least 4 hours under constant temperature and humidity condition (23±2° C.; relative Humidity: 50%±5%). If acclimation is not done for on-line real-time test, the temperature and humidity at that moment should be recorded while performing measurement, only for reference of comparison.

Set the testing procedure according to following test parameters:

Maximum test limit: 100 N;
Test speed: 254 mm/min;
Clamping distance: 51 mm;
Clamping pressure: 5 bars.

Fluid penetration speed was measured in accordance with EDANA 150.5-02.

Liquid penetration speed: when 5 ml 0.9% sodium chloride solution penetrates the sample, record the transit time of the liquid by circuit conductivity, in unit of second.

Tester: Lister liquid penetration instrument.

Fluid absorption was measured in accordance with EDANA 10.4-02.

Liquid absorption capability: after soaking the sample in liquid for a time duration of 10 minutes, the percentage of total weight increase is the absorption capability of the sample.

Liquid absorption capability: after soaking the sample in liquid for a time duration of 10 minutes, the total weight increase is the absorption capability of the sample. (g/g)

Retention: after soaking the sample in liquid for a time duration of 10 minutes, and keep it in a container for 2 minutes, then carefully place a 1976 g weight on the sample, the weight increase is the water retaining capacity of the sample. (g/g)

Rewet (g)

Place the sample to be tested on the absorption core (the 150 gsm SAP core (18% SAP) is applied during the test). Place a φ60 mm cylinder at the center position of the sample to be tested, take 15 ml brine and put it into the cylinder, and start the time counting at the same time, after 5 minutes, place many layers of filter paper with known weight on the surface of sample (till the top layer of filter paper does not absorb any liquid), and place a 1.2 kg standard pressing block on the filter paper at the same time, start to count the time again, remove the standard pressing block after a duration of 1 minute, weigh the mass of filter paper on the sample surface by means of a balance, its increased weight is the reverse osmosis value. The smaller the value, the better rewet performance will be expected.

Fluid holding capability was measured using the following procedure. A sample of the material was soaked in a liquid for a time duration of 10 minutes, and then kept in a container for 2 minutes. A 1976 g weight was then placed on the sample. The percentage of weight increase is the water retaining capacity of the sample.

Fluid Acquisition was measured in accordance with EDANA 150.5-02.

Acquisition: when 5 ml 0.9% sodium chloride solution penetrates the sample, record the transit time of the liquid by circuit conductivity, in unit of second.

Tester: Lister liquid penetration instrument.

Anti-reverse osmosis performance was measured in accordance with reference standards: EDANA 150.5-02, ERT 154.0-02.

Take a sample to be tested, place a φ60 mm cylinder at the center position of the sample to be tested, take 15 ml brine and put it into the cylinder, and start the time counting at the same time, after 5 minutes, place many layers of filter paper with known weight on the surface of sample (till the top layer of filter paper does not absorb any liquid), and place a 1.2 kg standard pressing block on the filter paper at the same time, start to count the time again, remove the standard pressing block after a duration of 1 minute, weigh the mass of filter paper on the sample surface by means of a balance, its increased weight is the reverse osmosis value. The smaller the value, the better the anti-reverse osmosis performance will be.

Suction range of liquid was measured with reference standard EDANA 10.4-02.

Liquid suction range: after one end of vertically suspended sample is soaked in the liquid for 5 minutes, the height that the liquid rises along the sample is the suction range of the sample.

Sample size: the sample size is 30 mm×200 mm

The sample is required to balance for at least 4 hours under constant temperature and humidity condition (23±2° C.; relative Humidity: 50%±5%).

Place the test stand into a plastic container, secure two rulers on the stand vertically, add 0.9% NaCl solution or distilled water (upon customer's request), adjust the liquid level to the scales on two rulers become 15 mm. Add and mix proper amount of blue coloring agent in the solution so as to make it easy to read. Rotate the rulers out of the liquid level, and wipe clean the water on the surface, fix the well prepared sample on the rulers by using fish tail clips, pay attention to align the lower end of the ruler with the zero point. Rotate the rulers out of the liquid level, and start count the time at the same time. Incline the end of the ruler extended into the liquid slightly backward to allow a certain gap between the ruler and the sample. At the same time the timer sounds after five minutes, rotate two rulers out of the liquid level and read the readings (observe the height that the liquid rises along the sample, read the value at peak point, if the individual value is too high on the sample edge, round it and read the value at other peak point). The test result is the actual value is subtracted by 15 mm, that is the value of liquid suction range.

Wicking rate: was measured in accordance with reference standard: EDANA 10.4-02.

After one end of vertically suspended sample is soaked in the liquid for 5 minutes, the height that the liquid rises along the sample is the suction range of the sample.

Sample size: the sample size is 30 mm×200 mm.

The sample is required to balance for at least 4 hours under constant temperature and humidity condition (23±2° C.; relative Humidity: 50%±5%).

Place the test stand into a plastic container, secure two rulers on the stand vertically, add 0.9% NaCl solution or distilled water (upon customer's request), adjust the liquid level to the scales on two rulers become 15 mm. Add and mix proper amount of blue coloring agent in the solution so as to make it easy to read. Rotate the rulers out of the liquid level, and wipe clean the water on the surface, fix the well prepared sample on the rulers by using fish tail clips, pay attention to align the lower end of the ruler with the zero point. Rotate the rulers out of the liquid level, and start count the time at the same time. Incline the end of the ruler extended into the liquid slightly backward to allow a certain gap between the ruler and the sample. At the same time the timer sounds after five minutes, rotate two rulers out of the liquid level and read the readings (observe the height that the liquid rises along the sample, read the value at peak point, if the individual value is too high on the sample edge, round it and read the value at other peak point). The test result is the actual value is subtracted by 15 mm, to provide the wicking rate.

The materials used in the composite sheets and comparative nonwoven fabrics are identified below. All percentages are weight percents unless indicated otherwise. All physical property and compositional values are approximate unless indicated otherwise.

"Pulp-1" refers to an untreated pulp staple fiber available from Weyerhaeuser under the product name NB416.

"Pulp-2" refers to a treated pulp staple fiber available from Weyerhaeuser under the product name NB405.

"PE/PET-1" refers to bicomponent staple fibers having a polyethylene sheath and a polyethylene terephthalate core, a fineness of 2.2 dtex, and an average length of 3 mm, which are available from Toray Chemical Korea Inc. under the product name EZBON A (UN-204).

"PE/PET-2" refers to eccentric bicomponent staple fibers having a polyethylene sheath and a polyethylene terephthalate core, having a fineness of 4.3 dtex, and an average length of 40 mm, which are available from IndoramaPolyester Industries Public Company Limited under the product name TS47.

"PE/PET-3" refers to bicomponent staple fibers having a polyethylene sheath and a polyethylene terephthalate core, having a fineness of 4.3 dtex, and an average length of 3 mm, available from Trevira under the product designation T255 staple fibers.

"PE/PP-1" refers to bicomponent staple fibers having a polyethylene sheath and a polypropylene core, a denier of 4.0, and an average length of 40 mm, which are available from Yangzhou Petrochemical Co. Ltd. under the product name Y116.

"PE/PP-2" refers to bicomponent staple fibers having a polyethylene sheath and a polypropylene core, a denier of 6.0, and an average length of 51 mm, which are available from JiangNan High Polymer Fiber under the product designation JNGX-PZ11-6*51L.

"PET-1" refers to polyethylene terephthalate staple fibers having a denier of 9.0, and an average length of 51 mm, which are available from IndoramaPolyester Industries Public Company Limited under the product designation INR-207Z-TG21/TG31.

"Latex" refers to an aqueous polymer dispersion produced from the monomers vinyl acetate and ethylene, which is available from Wacker under the product name VINNAPAS® 192. The Latex formulation has a solid constituent ranging from 51 to 53%.

In the Inventive Examples 1-4 set forth below, composite sheets in accordance with embodiments of the present invention were prepared by depositing 2-3 airlaid fabric layers overlying an air through bonded (ATB) carded fabric layer. The carded ATB fabrics used in Inventive Examples 1-4 are as follows.

"ATB-1" refers to a carded fabric comprising a mixture of staple fibers in which 30% by weight of the fibers comprise PE/PP-1 fibers and 70% by weight comprise PE/PET-2 fibers. The carded fabric had a basis weight of 30 g/m$^2$.

"ATB-2" refers to a carded fabric comprising a mixture of staple fibers in which 20% by weight of the fibers comprise PE/PP-1 fibers and 80% by weight comprise PE/PET-2 fibers. The carded fabric had a basis weight of 35 g/m$^2$.

"ATB-3" refers to a carded fabric comprising a mixture of staple fibers in which 20% by weight of the fibers comprise PET-1 fibers and 80% by weight comprise PE/PP-2 fibers. The carded fabric had a basis weight of 55 g/m$^2$.

INVENTIVE EXAMPLES

Unless otherwise indicated, the inventive examples were prepared according to the following procedures. In a first step, a previously prepared a fabric comprised of an air through bonded, carded nonwoven fabric (ATB fabric) was provided an unwound from a spool and transferred onto a continuous mesh belt. This ATB fabric defines the fluid acquisition layer, and hence, the fluid distribution component, of the composite sheet. The ATB fabric is then transported to the airlaid forming heads which deposit a mixture of cellulose and non-cellulose staple fibers onto the ATB fabric to form airlaid component of the composite sheet. In the following examples, 2 to 3 airlaid layers were deposited overlying the ATB fabric. The airlaid fabric layers were formed with a horizontal screen type forming technology with airlaid equipment available from M&J Company.

The cellulose and non-cellulose fibers of the airlaid layer(s) were homogeneously mixed using an air stream and a plurality of blades that create a turbulent flow within each forming head. A vacuum is positioned under the belt to assist in collecting the staple fibers onto the surface of the ATB fabric layer. After a first airlaid layer was deposited, a pre-stress roller was optionally positioned between the first and second forming heads. The composite sheet is then transported to the second airlaid forming area, where a second airlaid fabric layer is deposited overlying the previously deposited airlaid layer. This process is repeated until the desired amount of airlaid layers are deposited onto the composite sheet. The resulting composite sheet may then be stabilized with a heated roller that was heated to a temperature of 80 to 100° C. The composite sheet was then transported to, and passed through, a first heated oven, which was maintained at a temperature from about 120 to 150° C. The temperature of the first oven was selected to soften and melt the non-cellulose fibers of both the airlaid layers as well as the fluid acquisition layer (e.g., ATB layer) so that the fibers melt and flow together to form a coherent composite sheet.

Prior to passing through the oven, the composite sheet was transported to a coating station at which point a coating layer comprised of a latex formulation was deposited onto the surface of the outermost airlaid to form a coating layer. The composite sheet was then heated in an oven to dry and cure the latex coating. The oven was maintained at a temperature from about 120 to 150° C. Optionally, the composite sheet may further be dried in a third oven.

Inventive Example 1

Inventive Example 1 was prepared by depositing two airlaid layers onto a previously prepared fabric of ATB-1. The two airlaid layers comprised a homogenous fiber mixture of Pulp 1 fibers and PE/PET-1 fibers. Following deposition of the two airlaid layers, a coating of the Latex formulation was applied to the surface of the outermost airlaid layer. The composite sheet material was then successively passed through a series of ovens to bond the fibers to each other, and to dry and cure the Latex formulations. The dried add-on weight of the Latex layer was 2 weight percent, based on the total weight of Inventive Example 1. The resulting composite sheet had a basis weight of 70 g/m$^2$.

The composite sheet of Inventive Example 1 had structure as set forth in Table 1 below.

TABLE 1

Structure and composition of Composite Sheet of Inventive Example 1

| Layer | Materials | Percent of each layer in sheet (%) | Percent of each layer in sheet | Percent of each material per layer (%) | Basis weight (g/m$^2$) |
|---|---|---|---|---|---|
| Latex coating | Latex | 2.0 | 2.0 | 100% | 1.40 |
| Airlaid Layer 2 | Pulp-1 | 22.1 | 29.6 | 74.6 | 15.46 |
|  | PE/PET-1 | 7.5 |  | 25.4 | 5.25 |
| Airlaid Layer 1 | Pulp-1 | 18.1 | 25.6 | 70.7 | 12.65 |
|  | PE/PET-1 | 7.5 |  | 29.3 | 5.25 |
| ATB | ATB-1 | 42.9 | 42.9 | 100% | 30 |

Inventive Example 2

Inventive Example 2 was prepared by depositing two airlaid layers onto a previously prepared fabric of ATB-2. The two airlaid layers comprised a homogenous fiber mixture of Pulp 1 fibers and PE/PET-1 fibers. Following deposition of the two airlaid layers, a coating of the Latex formulation was applied to the surface of the outermost airlaid layer. The composite sheet material was then successively passed through a series of ovens to bond the fibers to each other, and to dry and cure the Latex formulations. The dried add-on weight of the Latex layer was 2 weight percent, based on the total weight of Inventive Example 2. The resulting composite sheet had a basis weight of 75 g/m$^2$.

The composite sheet of Inventive Example 1 had structure as set forth in Table 2 below.

TABLE 2

Structure and composition of Composite Sheet of Inventive Example 2

| Layer | Materials | Percent of each layer in sheet (%) | Percent of each layer in sheet | Percent of each material per layer (%) | Basis weight per layer (g/m$^2$) |
|---|---|---|---|---|---|
| Latex coating | Latex | 2.0 | 2.0 | 100% | 1.50 |
| Airlaid Layer 2 | Pulp-1 | 16.3 | 27.5 | 72.6 | 14.96 |
|  | PE/PET-1 | 7.5 |  | 27.4 | 5.65 |
| Airlaid Layer 1 | Pulp-1 | 19.9 | 23.9 | 68.4 | 12.65 |
|  | PE/PET-1 | 7.5 |  | 31.6 | 5.25 |
| ATB | ATB-2 | 46.7 | 46.7 | 100% | 35 |

Inventive Example 3

Inventive Example 3 was prepared by depositing two airlaid layers onto a previously prepared fabric of ATB-2. The two airlaid layers comprised a homogenous fiber mixture of Pulp 1 fibers and PE/PET-1 fibers. Following deposition of the two airlaid layers, a coating of the Latex formulation was applied to the surface of the outermost airlaid layer. The composite sheet material was then successively passed through a series of ovens to bond the fibers to each other, and to dry and cure the Latex formulations. The dried add-on weight of the Latex layer was 2 weight percent, based on the total weight of Inventive Example 3. The resulting composite sheet had a basis weight of 85 g/m$^2$.

The composite sheet of Inventive Example 3 had structure as set forth in Table 3 below.

TABLE 3

Structure and composition of Composite Sheet of Inventive Example 3

| Layer | Materials | Percent of each layer in sheet (%) | Percent of each layer in sheet | Percent of each material per layer (%) | Basis weight per layer (g/m$^2$) |
|---|---|---|---|---|---|
| Latex coating | Latex | 2.0 | 2.0 | 100% | 1.7 |
| Airlaid Layer 2 | Pulp-1 | 23 | 30.5 | 75.4 | 19.5 |
|  | PE/PET-1 | 7.5 |  | 24.6 | 6.38 |
| Airlaid Layer 1 | Pulp-1 | 18.8 | 26.3 | 71.5 | 16.0 |
|  | PE/PET-1 | 7.5 |  | 28.5 | 6.38 |
| ATB | ATB-2 | 41.2 | 41.2 | 100% | 35 |

Inventive Example 4

Inventive Example 4 was prepared by depositing three airlaid layers onto a previously prepared fabric of ATB-3. The three airlaid layers comprised a homogenous fiber mixture of Pulp 1 fibers and PE/PET-1 fibers. Following deposition of the three airlaid layers, a coating of the Latex formulation was applied to the surface of the outermost airlaid layer. The composite sheet material was then successively passed through a series of ovens to bond the fibers to each other, and to dry and cure the Latex formulations. The dried add-on weight of the Latex layer was 2 weight percent, based on the total weight of Inventive Example 4. The resulting composite sheet had a basis weight of 95 g/m$^2$.

The composite sheet of Inventive Example 4 had structure as set forth in Table 4 below.

TABLE 4

Structure and composition of Composite Sheet of Inventive Example 4

| Layer | Materials | Percent of each material in sheet (%) | Percent of each layer in sheet | Percent of each material per layer (%) | Basis weight (g/m$^2$) |
|---|---|---|---|---|---|
| Latex coating | Latex | 2.0 | 2.0 | 100% | 1.9 |
| Airlaid Layer 3 | Pulp-1 | 10.5 | 13.1 | 80.2 | 10.01 |
|  | PE/PET-1 | 2.6 |  | 19.8 | 2.47 |
| Airlaid Layer 2 | Pulp-1 | 10.5 | 14.1 | 74.5 | 10.01 |
|  | PE/PET-1 | 3.6 |  | 25.5 | 3.42 |
| Airlaid Layer 1 | Pulp-1 | 9.0 | 12.8 | 70.4 | 8.58 |
|  | PE/PET-1 | 3.8 |  | 29.6 | 3.61 |
| ATB | ATB-2 | 57.9 | 57.9 | 100% | 55 |

Comparative Examples

Comparative Examples 1-3

Comparative Examples 1-3 were airlaid nonwoven fabrics having basis weights of 70, 80 and 95 g/m$^2$, respectively. The nonwoven fabrics comprised a blend of Pulp 1 staple fibers and PE/PET-3 staple fibers. A latex formulation of the Latex was applied to the each of Comparative Examples 1-3 as an as dried amount of 6.0%, 6.0%, and 6.5 weight %, respectively, based on total weight of each of the fabrics. Comparative Example 1 included 71% Pulp 1 fibers and 23% PE/PET-3 fibers; Comparative Example 2 included 70% Pulp 1 fibers and 24% PE/PET-3 fibers; and Comparative Example 3 included 73.5% Pulp 1 fibers and 20% PE/PET-3 fibers. The fabrics were dried in one or more ovens at temperatures from 150 to 160° C. The fabrics of Comparative Examples 1-3 were provided by Fitesa China Airlaid Co. Ltd. of Tianjin, China.

Comparative Examples 4-5

Comparative Example 4 comprised an air through bonded (ATB) nonwoven fabric with a basis weight of 40 g/m$^2$, and comprised of a fiber mixture of 20 weight % PE/PP-1 fibers and 80 weight % PE/PET-2 staple fibers. Comparative Example 5 comprised an ATB nonwoven fabric with a basis weight of 55 gsm, and comprised of a fiber mixture of 20 weight % PET-1 fibers and 80 weight % PE/PP-2 staple fibers.

Comparative Example 6

Comparative Example 6 comprised a nonwoven fabric comprised of PET resin bonded fibers with a basis weight of 45 g/m$^2$.

Comparative Examples 7-9

Comparative Examples 7-9 were spunbond fabrics having a basis weights of 50, 60, and 70 g/m², respectively. The spunbond fabrics were comprised of polypropylene continuous filaments that included 0.5 weight % $TiO_2$ as a whitener. The filaments were calender bonded with a calendering roll having an oval/elliptical 18% bonding pattern at a temperature of about 160° C. The fabrics of Comparative Examples 7-9 were obtained from Shandon Kanjie Nonwovens.

Comparative Examples 10-11

The nonwoven fabrics of Comparative Examples 10 and 11 were spunlace nonwoven fabrics with basis weights of 50 g/m² and 70 g/m², respectively. Comparative Example 10 comprised 50% by weight of PET fibers having a fineness of 1.67 dtex, and 50% by weight of viscose fibers having a fineness of 1.67 dtex and lengths of 38 mm. Comparative Example 11 comprised 50% by weight of PET fibers (antimony free) having a fineness of 1.67 dtex, and 50% by weight of viscose fibers having a fineness of 1.67 dtex and lengths of 38 mm.

Inventive Examples 1-4 and comparative Examples 1-11 were evaluated for properties desirable for use as an acquisition/fluid acquisition layer in the construction of absorbent articles. As discussed previously, it is desirable for such fabrics/materials to exhibit a good balance of properties including acquisition, absorption, and retention of fluids. It is also desired that the fabric have good fluid wicking properties which will permit the fluid to be distributed throughout the composite sheet prior to being transported into the core. In addition, resiliency of the fabric (i.e., composite sheet) is desirable to provide comfort to the wearer. To show the suitability for the inventive composite sheets for use in absorbent articles, these properties were all evaluated. The results are summarized in Table 5 below.

Inventive Example 5

Inventive Example 5 was prepared in accordance with the procedures discussed above. The fluid acquisition layer comprised an air through bonded carded fabric with a basis weight of about 20 g/m², and comprised 30% by weight of the fibers comprise PE/PP-1 fibers and 70% by weight comprise PE/PET-2 fibers. The first airlaid layer comprised 79.31% Pulp-1 staple fibers and 20.69% by weight of PE/PET-1 staple fibers. The basis weight of the airlaid layer was about 50 g/m². The two layered composite sheet material had a thickness of about 1 mm. The overall basis weight of the composite sheet was 70 g/m². An emulsion coating comprised of the Latex formulation was sprayed onto the outer surface of the airlaid fabric. Table 6 below summarizes the structure and composition of the composite sheet of Inventive Example 5.

TABLE 6

Composition of Inventive Example 5

| | Carded ABT fabric | Cellulose staple fiber | Bicomponent staple fiber | Latex |
|---|---|---|---|---|
| Fluid acquisition layer | 100.00% | 0% | 0% | 0% |
| First fiber layer | 0% | 79.31% | 20.69% | 0% |
| 2% emulsion here indicates the percentage of mass in total determined mass of the product | | | | 2.00% |

Inventive Example 6

Inventive Example 6 comprised a three layered composite sheet having a basis weight of about 85 g/m², and a thickness of about 1.75 mm. The fluid acquisition layer comprised a carded ATB fabric comprising 30% by weight of the fibers comprise PE/PP-1 fibers and 70% by weight comprise PE/PET-2 fibers, and with a basis weight of 35 g/m². The airlaid component of the composite sheet comprised two airlaid layers that were deposited successively overlying the fluid acquisition layer. Both airlaid layers comprised a blend of Pulp-1 staple fibers and PE/PET-1 staple fibers. An emulsion coating comprised of the Latex formulation was sprayed onto the outer surface of the airlaid fabric at a dried add-on amount of about 2 weight percent. Inventive Example 6 was prepared in accordance with the process steps discussed above. Table 7 below summarizes the structure and composition of the composite sheet of Inventive Example 6.

The structure of the composite quick-permeable airlaid paper is comprised of three layers, the determined mass of quick-permeable acquisition distribution layer takes about 41.20% of total determined mass of the product, the determined mass of the first fiber layer takes about 26.34% of total determined mass of the product, the determined mass for the fiber layer takes about 30.46% of the total determined weight of the product, the latex takes about 2.00% of the total determined weight of the product. The distribution of various components at various layers is given in Table 7 below, the ratio in the table is expressed by the percentage of mass of various materials at the layer.

TABLE 7

Composition of Inventive Example 6

| | Carded ABT fabric | Cellulose staple fiber | Bicomponent staple fiber | Latex |
|---|---|---|---|---|
| Fluid acquisition layer | 100.00% | 0% | 0% | 0% |
| First airlaid layer | 0% | 71.51% | 28.49% | 0% |
| Second airlaid layer | 0% | 75.36% | 24.64% | 0% |
| 2% emulsion here indicates the percentage of mass in total determined mass of the product | | | | 2.00% |

Inventive Example 7

Inventive Example 7 comprised a four layered composite sheet having a basis weight of about 140 g/m², and a thickness of about 3.10 mm. The fluid acquisition layer comprised a carded of ATB-3 with a basis weight of 55 g/m². The airlaid component of the composite sheet comprised three airlaid layers that were deposited successively overlying the fluid acquisition layer. The first airlaid layer comprised a blend of Pulp-2 staple fibers and PE/PET-1 staple fibers. The second and third airlaid layers comprised a blend of Pulp-1 staple fibers and PE/PET-1 staple fibers. An emulsion coating comprised of the Latex formulation was sprayed onto the outer surface of the airlaid fabric at a dried add-on amount of about 2 weight percent. Inventive Example 7 was prepared in accordance with the process steps discussed above. Table 8 below summarizes the structure and composition of the composite sheet of Inventive Example 7.

The structure of the composite quick-permeable airlaid paper is comprised of three layers, the determined mass of quick-permeable acquisition distribution layer takes about 41.20% of total determined mass of the product, the determined mass of the first fiber layer takes about 26.34% of total determined mass of the product, the determined mass for the fiber layer takes about 30.46% of the total determined weight of the product, the latex takes about 2.00% of the total determined weight of the product. The distribution of various components at various layers is given in Table 8 below, the ratio in the table is expressed by the percentage of mass of various materials at the layer.

The fluid acquisition layer comprised about 39.29 weight % of the composite sheet, based on the total weight of the composite sheet. The first, second, and third airlaid layers comprised about 16.07%, 21.43%, and 21.43%, respectively, based on the total weight of the composite sheet. A layer of the Latex was applied at a dried add-on amount of about 1.79%, based on the total weight of the composite sheet. The use of Pulp-2 (treated pulp) in the first airlaid provides several benefits, such as a much softer and fluffier effect, and which also allows the first airlaid layer to form density gradient with the second and third airlaid layers.

TABLE 8

Composition of Inventive Example 7

| | Carded ABT fabric | Cellulose staple fiber Pulp-1 | Cellulose staple fiber Pulp-2 | Bicomponent staple fiber | Latex |
|---|---|---|---|---|---|
| Fluid acquisition layer | 100.00% | 0% | 0% | 0% | 0% |
| First airlaid layer | 0% | 0% | 66.67% | 33.33% | 0% |
| Second airlaid layer | 0% | 75.00% | 0% | 25.00% | 0% |
| Third airlaid layer | 0% | 75.00% | 0% | 25.00% | 0% |
| 2% emulsion here indicates the percentage of mass in total determined mass of the product | | | | | 1.79% |

Inventive Example 8

In this example, an inventive composite sheet is prepared in accordance with the structure of the composite sheet of Inventive Example 6. However, in this example, a plurality of alternating ridges and valleys is created on the outer surface of the outermost airlaid layer (e.g., third airlaid layer) by passing the sheet material in contact with a roll having a patterned surface. During this step, pressure and heat are applied to form a plurality of alternating ridges and grooves that extend longitudinally along the machine direction length of the composite sheet. The surface of the pattern roll comprises a plurality of grooves/channels having a depth (e.g., 1 mm), and that are spaced apart from adjacent grooves/channels (e.g., a spacing of 3 mm). The plurality of grooves/channels extend circumferentially around the surface of the roll. The temperature of the pattern roll is preferably not more than 120° C. The pressure applied by the patterned roll to the outermost airlaid layer can be adjusted according to the desired depth, which is generally not more than 60 Nmm, of the grooves/stripes formed on the outer surface of the composite sheet. Adjustment to temperature and pressure can be done according to the requirement of the end products. The products with grooves/stripes can be obtained by the subsequent processing process after the composite sheet is embossed.

In the following comparative Examples (Comparative Examples 12-14) the same processes as described above were used in making the fabrics.

Comparative Example 12

Comparative Example 12 comprised an airlaid fabric having a basis weight of about 80 g/m², and a thickness of about 1.3 mm. The fabric was prepared by depositing three airlaid fabric layers overlying a paper substrate layer. Suitable materials for the paper substrate layer may include NKA130 series made by Golden HongYe Paper or 17 gsm products made by Havix.

The airlaid fabric comprised a blend of cellulose staple fibers and non-cellulose bicomponent PLA fibers. The following materials may be used for the cellulosic fibers in the airlaid layers: Pulp-1 (Weyerhauser NB416), International Paper Super soft M, or Georgia Pacific 4821, 4822, 4823 and mixtures thereof. The cellulose fibers generally have a fiber length that is about 2 to 5 mm. The non-cellulose staple fibers comprised bicomponent fibers having a PLA sheath and a PLA core. The fineness of PLA/PLA bicomponent fibers were 2.2 dtex/6 mm. The melting point temperature of the PLA polymer of the sheath was about 130° C., and the melting point temperature of the PLA polymer of the core was about 160° C.

The structure of the airlaid fabric was comprised of four layers, the determined mass of the first layer takes about 16% of total determined mass of the product, the determined mass of the second layer takes about 23% of total determined mass of the product, the determined mass for the third layer takes about 29% of the total determined weight of the product, the determined mass for the third layer takes about 32% of the total determined weight of the product. Both sides of the material were sprayed with water at 10% of total determined mass during the process.

The distribution of various components at various layers is given in Table 9 below.

TABLE 9

Composition of Comparative Example 12.

| | Lining (13 gsm) | Cellulosic fiber | PLA/PLA bicomponent fiber |
|---|---|---|---|
| Paper substrate layer | 100% | 0% | 0% |
| First airlaid layer | 0% | 60% | 40% |
| Second airlaid layer | 0% | 45% | 55% |
| Fourth layer | 0% | 0% | 100% |

Comparative Example 13

Comparative Example 13 comprised a 4-layer fabrics having a basis weight of about 150 g/m², and a thickness of about 1.3 mm. The same materials as in Comparative Example 12 were used in Comparative Example 13. The paper substrate layer had a basis weight of 17 g/m².

The structure of the airlaid paper was comprised of four layers, the determined mass of the first layer takes about 11% of total determined mass of the product, the determined mass of the second layer takes about 25% of total determined mass of the product, the determined mass for the third layer takes about 31% of the total determined weight of the product, the determined mass for the third layer takes about 33% of the total determined weight of the product. And both sides of the material were sprayed with water of 10% of total determined mass during the process. The distribution of various components at various layers is given in Table 10 below.

TABLE 10

Composition of Comparative Example 13.

|  | Lining (17 gsm) | Cellulosic fiber | PLA/PLA Composite fiber |
|---|---|---|---|
| Paper substrate layer | 100% | 0% | 0% |
| First airlaid layer | 0% | 70% | 30% |
| Second airlaid layer | 0% | 50% | 50% |
| Fourth layer | 0% | 0% | 100% |

Comparative Example 14

Comparative Example 14 comprised a 4-layer fabric having a basis weight of about 150 g/m², and a thickness of about 1.3 mm. The same materials as in Comparative Example 12 were used in Comparative Example 13. The paper substrate layer had a basis weight of 17 g/m².

The total determined mass of this embodiment's airlaid paper is about 175 g/m², and the thickness was about 1.45 mm. The cellulose fibers in the airlaid layer comprised Pulp-1 staple fibers with fiber lengths of about 2-5 mm. The bi-component staple fibers were comprised of a core of polypropylene (PP), and a sheath of polyethylene (PE). The fiber lengths were about 3-6 mm, and the fineness was about 1.7-3.0 dtex.

The base nonwoven fabric layer had a basis weight of 22 g/m², and comprised a polypropylene spunbonded nonwoven fabric. The super absorbent polymer was from Sandia-930, or from manufacturers as Stockhausen, Sumitomo, Shokubai and etc., the fourth layer in was a latex coating that was a sprayed on latex emulsion comprised of the Latex formulation discussed above.

The structure of the fabric of Comparative Example 14 comprised of four layers. The determined mass of the first layer takes about 12.6% of total determined mass of the product, the determined mass of the second layer takes about 27.4% of total determined mass of the product, the determined mass for the third layer takes about 30% of the total determined weight of the product, the determined mass for the forth layer takes about 28% of the total determined weight of the product, and the emulsion of 32% of the total amount will be sprayed on the forth layer. The distribution of various components at various layers is given in Table 11 below.

TABLE 11

Composition of Comparative Example 14.

|  | Cellulosic fiber | Lining non-woven fabrics (22 gsm) | Super absorbent polymer (SAP) | Polyethylene powder | Bicomponent Composite fiber |
|---|---|---|---|---|---|
| Base nonwoven fabric layer | 0% | 100% | 0% | 0% | 0% |
| Second layer | 62% | 0% | 0% | 25.5% | 12.5% |
| Third layer | 50% | 0% | 50% | 0% | 0% |
| Forth layer | 62% | 0% | 25% | 0% | 13% |

The emulsion of 2% of the total amount will be sprayed on the forth layer

In Table 12, below, Inventive Examples 5-8 were evaluated and compared to Comparative Examples 12-14. With respect to the blind testing, 20 individuals were randomly selected to evaluate the softness, fluffiness of material by their feeling and the dry and crisp properties of the material after testing the reverse osmosis performance. In general, the more softer and fluffier the nonwoven fabric, the drier the surface of the fabric will be expected.

It can be seen from the data in Table 12 that, the inventive composite sheet exhibited much better performance; this is particularly true for reverse osmosis performance. The product with alternating grooves/channels exhibited better diffusivity, such as suction range (in length wise direction that is the direction of the stripes) increases by one time, which also is the main cause why the diffusion aspect ratio of the liquid is far more than 1. Thus, it is expected that use of the composite sheets as the distribution layer of absorbent articles can fully utilize the effective area of the absorption layer under the distribution layer, minimize the investment on raw materials, and reduce the cost of production.

In addition, it can be seen by comparison of Table 12, the products of present invention is fluffier (lower density) and the dry and crisp properties has been improved significantly, and the material has very good rebound resilience, and is a kind of superior quality quick-permeable airlaid paper. Even after the grooves/channels are embossed, the article was still fluffier (lower density) than the airlaid papers of the prior art, and both the reverse osmosis performance and dry and crisp properties are also very good. This represents a significant improvement in comparison with the past art, and as the material has very good rebound resilience, it is a kind of superior quality quick-permeable airlaid paper.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of preparing a composite sheet, comprising:
   providing a carded nonwoven fabric, the carded nonwoven fabric comprising staple fibers;
   depositing a first airlaid layer onto a surface of the carded nonwoven fabric to form a composite sheet, the first airlaid layer comprising a mixture of cellulose staple fibers and non-cellulose staple fibers comprising a polymer; and air through bonding the composite sheet, with heated gas, to cause the polymer of the non-cellulose staple fibers of the first airlaid layer to melt and fuse with adjacent staple fibers of the fabric, adjacent fibers of the cellulose staple fibers and adjacent fibers of the non-cellulose staple fibers, wherein the non-cellulose staple fibers of the airlaid layer are bonded to each other, to the cellulose staple fibers, and to the staple fibers of the carded nonwoven fabric, and wherein a basis weight of the composite sheet is from about 40 to 225 g/m², and the composite sheet having a fluid acquisition time ranging from about 0.5 seconds to about 2 seconds;
    a fluid absorption ranging from about 15 to 30 g/g;
    a fluid retention ranging from about 8 to 15 g/g;
    a fluid wicking height ranging from about 10 to 50 mm; and
    a resiliency ranging from about 30 to 60%.

2. The method according to claim 1, wherein providing the carded nonwoven fabric comprises preparing the carded nonwoven fabric on a carded fabric forming device disposed upstream of a device for depositing said first airlaid layer.

3. The method according to claim 1, further comprising a step of air through bonding the staple fibers of the carded nonwoven fabric prior to depositing the first airlaid layer onto the carded nonwoven fabric.

4. The method according to claim 1, wherein air through bonding the composite sheet further comprises air through bonding of the staple fibers of the carded nonwoven fabric to each other.

5. The method according to claim 1, further comprising successively depositing a plurality of airlaid layers onto said first airlaid layer.

6. The method according to claim 1, wherein the composite sheet comprises from 2 to 10 airlaid layers successively deposited overlying the carded nonwoven fabric.

7. The method according to claim 1, wherein the carded nonwoven fabric comprises bicomponent staple fibers having a sheath of a first polymer component and a core of a second polymer component.

8. The method of claim 7, wherein the first and second polymer components comprise the same polymer.

9. The method of claim 7, wherein the sheath comprises polyethyelene and the core comprises polypropylene or polyethylene terephthalate, and mixtures thereof.

10. The method according to claim 1, wherein the staple fibers of the carded nonwoven fabric having a length from about 20 to 100 millimeters.

11. The method according to claim 1, wherein the composite sheet comprises one or more airlaid layers including cellulose staple fibers and non-cellulose staple fibers, and the method further comprising mixing a super absorbent polymer or super absorbent fibers with the cellulose staple fibers and the non-cellulose staple fibers of at least one or more of the airlaid layers.

12. The method according to claim 1, wherein the carded nonwoven fabric comprises bicomponent staple fibers having a polyethyelene sheath and a polypropylene or polyethylene terephthalate core, and mixtures thereof, and the non-cellulose staple fibers comprise bicomponent staple fibers having a polyethyelene sheath and a polypropylene or polyethylene terephthalate core, and mixtures thereof.

13. The method according to claim 1, wherein the staple fibers of the carded nonwoven fabric comprise bicomponent filaments having a sheath and core configuration in which the sheath comprises a polyethylene terepthalate, and the core comprises polyethylene terepthalate having a melting temperature higher than a melting temperature of the polyethylene terepthalate comprising the sheath.

14. The method according to claim 1, wherein the staple fibers of the carded nonwoven fabric comprising a sustainable polymer, and the non-cellulose staple fibers of the first airlaid layer comprises a sustainable polymer.

15. The method according to claim 14, wherein the staple fibers of the carded nonwoven fabric comprise bicomponent filaments having a sheath and core configuration in which the sheath comprises a polylactic acid polymer, and the core comprises polylactic acid having a melting temperature higher than a melting temperature of the polylactic acid comprising the sheath.

16. The method according to claim 1, further comprising a step of depositing a coating layer of a polymeric latex on a surface of an outermost airlaid layer, and then heating the composite sheet to a temperature sufficient to cure and dry the polymeric latex.

17. The method according to claim 1, further comprising forming a plurality of alternating ridges and channels that extend across an outer surface of an outermost airlaid layer of the composite sheet.

18. A method of preparing a composite sheet, comprising:
    depositing a plurality of non-cellulose staple fibers onto a collection surface to form a first nonwoven fabric layer;
    depositing a first airlaid layer onto a surface of the first nonwoven fabric layer, the first airlaid layer comprising a mixture of cellulose staple fibers and non-cellulose staple fibers; and
    bonding the staple fibers of the first nonwoven fabric layer to the cellulose staple fibers and the non-cellulose staple fibers of the first airlaid layer to form a coherent composite sheet, and wherein the composite sheet is characterized by the following:
    a fluid acquisition time ranging from about 0.5 seconds to about 2 seconds;
    a fluid absorption ranging from about 15 to 30 g/g;
    a fluid retention ranging from about 8 to 15 g/g;
    a fluid wicking height ranging from about 10 to 50 mm; and
    a resiliency ranging from about 30 to 60%.

19. The method of claim 18, wherein bonding comprises air through bonding with heated gas, to cause a polymer of the non-cellulose staple fibers of the first airlaid layer to melt and fuse such that the non-cellulose staple fibers of the first airlaid layer are bonded to each other and to, the cellulose staple fibers, and to the non-cellulose staple fibers.

* * * * *